US012697606B2

(12) United States Patent
Liu et al.

(10) Patent No.: US 12,697,606 B2
(45) Date of Patent: Aug. 4, 2026

(54) METHOD OF PREPARING ELECTROCATALYSTS FOR CONVERTING CARBON DIOXIDE TO CHEMICALS

(71) Applicants: UCHICAGO ARGONNE, LLC, Chicago, IL (US); BOARD OF TRUSTEES OF NORTHERN ILLINOIS UNIVERSITY, DeKalb, IL (US)

(72) Inventors: Di-Jia Liu, Elmhurst, IL (US); Tao Xu, Naperville, IL (US); Jianxin Wang, Chicago, IL (US)

(73) Assignees: UCHICAGO ARGONNE, LLC, Chicago, IL (US); BOARD OF TRUSTEES OF NORTHERN ILLINOIS UNIVERSITY, DeKalb, IL (US)

( * ) Notice: Subject to any disclaimer, the term of this patent is extended or adjusted under 35 U.S.C. 154(b) by 639 days.

(21) Appl. No.: 18/097,439

(22) Filed: Jan. 16, 2023

(65) Prior Publication Data

US 2023/0278014 A1 Sep. 7, 2023

Related U.S. Application Data

(63) Continuation-in-part of application No. 17/008,853, filed on Sep. 1, 2020, now Pat. No. 11,554,363.

(51) Int. Cl.
B01J 23/78 (2006.01)
B01J 23/14 (2006.01)
(Continued)

(52) U.S. Cl.
CPC ............... B01J 23/78 (2013.01); B01J 23/14 (2013.01); B01J 23/72 (2013.01); B01J 35/618 (2024.01);
(Continued)

(58) Field of Classification Search
CPC . B01J 23/78; B01J 35/618; B01J 23/14; B01J 23/72; B01J 23/835; B01J 37/0081;
(Continued)

(56) References Cited

U.S. PATENT DOCUMENTS 3,625,768 A 12/1971 Moulton et al.
4,201,760 A 5/1980 Arendt et al.
(Continued)

FOREIGN PATENT DOCUMENTS

CN 117418269 A * 1/2024 ......... H01M 4/9041
WO WO-2013/166505 A2 11/2013

OTHER PUBLICATIONS

Abbasi, et al., "Tailoring the Edge Structure of Molybdenum Disulfide toward Electrocatalytic Reduction of Carbon Dioxide," ACS Nano 11(1), pp. 453-460 (2017).
(Continued)

*Primary Examiner* — Patricia L. Hailey
(74) *Attorney, Agent, or Firm* — Foley & Lardner LLP

(57) ABSTRACT

Electrocatalysts composed of single atoms or metal clusters dispersed over porous carbon support were prepared by a lithium-melt method. The new catalysts demonstrated high selectivity, high Faradic efficiency and low overpotential toward to the electrocatalytic reduction of carbon dioxide to chemicals such as glycerol or isopropanol.

19 Claims, 13 Drawing Sheets

(51) Int. Cl.

| | |
|---|---|
| *B01J 23/72* | (2006.01) |
| *B01J 35/61* | (2024.01) |
| *B01J 37/00* | (2006.01) |
| *B01J 37/02* | (2006.01) |
| *B01J 37/04* | (2006.01) |
| *C07C 29/154* | (2006.01) |

(52) U.S. Cl.
CPC ....... *B01J 37/0081* (2013.01); *B01J 37/0228* (2013.01); *B01J 37/04* (2013.01); *C07C 29/154* (2013.01)

(58) Field of Classification Search
CPC ....... B01J 37/0228; B01J 37/04; C07C 31/10; C07C 31/225; C07C 29/154; C25B 3/26
USPC ......................... 502/300, 352, 353, 355, 182
See application file for complete search history.

(56) References Cited

U.S. PATENT DOCUMENTS

| | | | |
|---|---|---|---|
| 5,071,815 | A | 12/1991 | Wallace et al. |
| 10,844,501 | B2 | 11/2020 | Liu et al. |
| 10,978,718 | B2 | 4/2021 | Liu et al. |
| 2014/0291161 | A1 | 10/2014 | Awazu et al. |
| 2015/0311522 | A1 | 10/2015 | Fang et al. |
| 2019/0067706 | A1 | 2/2019 | Liu et al. |
| 2019/0276943 | A1 | 9/2019 | Liu et al. |
| 2021/0202955 | A1 | 7/2021 | Liu et al. |
| 2022/0062864 | A1* | 3/2022 | Liu ........................ C25B 11/091 |

OTHER PUBLICATIONS

Ahmed & Mao, "Ultrafine Iridium Oxide Nanorods Synthesized by Molten Salt Method toward Electrocatalytic Oxygen and Hydrogen Evolution Reactions," Electrochimica Acta 212, pp. 686-693 (2016).

Barkholtz, et al., "Lithium Assisted 'Dissolution-Alloying' Synthesis of Nanoalloys from Individual Bulk Metals," Chemistry of Materials 28(7), pp. 2267-2277 (2016).

Calvinho, et al., "Selective CO2 reduction to C3 and C4 oxyhydrocarbons on nickel phosphides at overpotentials as low as 10 mV," Energy & Environmental Science 11, pp. 2550-2559 (2018).

Duan, et al., "Amorphizing of Cu Nanoparticles toward Highly Efficient and Robust Electrocatalyst for CO2 Reduction to Liquid Fuels with High Faradaic Efficiencies," Advanced Materials 30(14), 1706194, 7 pages (2018).

Kim, et al., "Copper nanoparticle ensembles for selective electroreduction of CO2 to C2—C3 products," Proceedings of the National Academy of Sciences 114(40), pp. 10560-10565 (2017).

Lin, et al., "Direct Synthesis of Bimetallic Pd3Ag Nanoalloys from Bulk Pd3Ag Alloy," Inorganic Chemistry 51(24), pp. 13281-13288 (2012).

Mugavero, et al., "Materials discovery by crystal growth: Lanthanide metal containing oxides of the platinum group metals (Ru, Os, Ir, Rh, Pd, Pt) from molten alkali metal hydroxides," Journal of Solid State Chemistry 182(7), pp. 1950-1963 (2009).

Ramierez-Valencia, et al., "From CO2 to Value-Added Products: A Review about Carbon-Based Materials for Electro-Chemical CO2 Conversion," Catalysts 11(3):351, 67 pages (2021).

Wang, et al., "CO2 reduction to acetate in mixtures of ultrasmall (Cu)n,(Ag)m bimetallic nanoparticles," Proceedings of the National Academy of Sciences 115(2), pp. 278-283 (2018).

Xu, et al., "Highly selective electrocatalytic CO2 reduction to ethanol by metallic clusters dynamically formed from atomically dispersed copper," Nature Energy 5, pp. 623-632 (2020).

Xu, et al., "Supplemental Information—Synthesis of Supported Platinum Nanoparticles from Li—Pt Solid Solution," Journal of the American Chemical Society 132(7), 8 pages (2010).

Xu, et al., "Synthesis of Supported Platinum Nanoparticles from Li—Pt Solid Solution," Journal of the American Chemical Society 132(7), pp. 2151-2153 (2010).

Yang, et al., "Atomically dispersed Ni(I) as the active site for electrochemical CO2 reduction," Nature Energy 3, pp. 140-147 (2018).

* cited by examiner

METHOD OF PREPARING ELECTROCATALYSTS FOR CONVERTING CARBON DIOXIDE TO CHEMICALS

CROSS-REFERENCE TO RELATED APPLICATIONS

This application is a continuation-in-part of U.S. patent application Ser. No. 17/008,853, filed Sep. 1, 2020 (now U.S. Pat. No. 11,554,363), the contents of which is incorporated herein by reference in its entirety.

GOVERNMENT SUPPORT CLAUSE

This invention was made with government support under Contract No. DE-AC02-06CH11357 awarded by the United States Department of Energy to UChicago Argonne, LLC, operator of Argonne National Laboratory. The government has certain rights in the invention.

TECHNICAL FIELD

The present disclosure relates generally to methods and materials relating to electrocatalysts for carbon dioxide ("$CO_2$") reduction.

BACKGROUND

Carbon dioxide emissions have been increasing nearly continuously since the dawn of the industrial revolution. The amount of $CO_2$ in the atmosphere has been associated with an increasing number of issues, including breathable air quality for humans and global warming via the greenhouse effect. Therefore, there is an increasing desire to reduce $CO_2$ from waste streams or to remove $CO_2$ from the atmosphere. Chemical or electrochemical conversion of $CO_2$ into useful chemicals and fuels represent very attractive ways to address $CO_2$ emission, particularly where low-cost renewable energy sources, such as wind and solar, are available.

However, conventional methods of converting $CO_2$ to fuels typically apply heterogeneous catalysis in a gas phase, a complex and energy-intensive process. Such heterogeneous catalysis requires an elevated temperature and typically high pressure. For example, $CO_2$ can be catalytically converted to carbon monoxide ("CO") in the presence of hydrogen and a catalyst through a reverse water-gas shift reaction at a temperature above 200° C. $CO_2$ can also be catalyzed to methanol over $Cu/ZnO/Al_2O_3$ in the presence of hydrogen under very high pressure (50-100 bar). High temperature and high pressure relative to ambient adds complexity and cost to the conversion system and manufacturing process. Ideally, $CO_2$ reduction catalysts would operate under low temperatures and low pressure and yield high amounts of product. Current catalysts are best used at high temperatures, creating a safety risk.

One possible approach is the electrocatalytic reduction of $CO_2$. Electrocatalytic reduction offers the benefit of converting $CO_2$ to fuels at ambient temperature and pressure in the aqueous phase. However, in general, conversion can only occur in the presence of electrocatalysts. Typically, the electrocatalyst is composed of catalytically active sites supported over a conductive substrate, such as carbon. Although such electrocatalysts can operate in both aqueous and organic solvents, the nature of their catalytic activity requires that during the reduction, $CO_2$ adsorbed on the catalyst surface will capture the electrons and protons in the electrolyte to form hydrocarbons as useful products. The catalytic reactions generally take place on the surface and inside of the pores of the catalyst material. Therefore, highly porous catalysts can offer more catalytic surface area per volume. The microporosity of the catalyst complicates the overall reaction pathways due to the need for reactants and products to diffuse in/out of the pores. For example, the microporosity will increase the carbon dioxide retention time inside of a porous carbon support, which could potentially alter the reaction pathways and products.

In keeping with this desire for electrocatalysts, a number of $CO_2$ reduction reaction ("$CO_2RR$") electrocatalysts have been developed. Such electrocatalysts are often synthesized through a wet chemistry method by depositing solvated ionic metal precursors over a conductive support through an aqueous or non-aqueous solution, followed by a chemical or thermal reduction to convert the metal from ionic to metallic form. Another approach is to electroplate the metal directly over the substrate by applying the reducing potential to the conductive support where metal ion is reduced to metal by capturing the electron. The main challenge of these approaches is the lack of control of uniform size of catalytic centers or metal particle sizes. The catalytic active centers from these syntheses are often composed of bulk materials, nanomaterials, or multi-atom islands. Particularly, it is extremely difficult to reduce the metal active site down to single atom level. It is also very difficult to systematically produce uniform metal particle size which has a direct impact to the selectivity of $CO_2$ to chemical conversion. The inadequacy of conventional methods in reducing catalyst particles down to single atom or near single atom size of cluster render them inefficient to convert $CO_2$ to a specific chemical with high selectivity. The lack of control of metal particle size by the conversion methods also makes it difficult to alter conversion product output since the $CO_2$ reduction reaction pathway is often determined by the dimension of the metal active center. The current $CO_2$ reduction reaction electrocatalyst technology has the disadvantages of low selectivity, low efficiency, and low stability.

Another challenge relating to electroplating stems from the inability to benefit from the morphology of the underlying support. Similar to any electrocatalytic system, the specific surface area and porosity of the support materials, such as carbon, could have major impacts on the $CO_2$ reduction reaction conversion product. This is primarily due to the porosity which can lead to different surface retention time, thus changing the reaction path and final product.

For electrocatalytic conversion of $CO_2$ to fuel or chemicals, it is preferable that the conversion be highly selective under controlled conditions, such as voltage, so that no additional product separation is needed. Furthermore, the onset voltage should be as close to the theoretical potential as possible in order to reduce the electricity cost of the $CO_2RR$ process. The prior art catalysts do not have near to 100% selectivity toward one single product, or capability of producing hydrocarbon chemicals with two or more carbon atom products (e.g., $C_2$, $C_3$). For example, no prior process provides high selectivity toward isopropanol, a C3 product. The efficiency or Faradaic efficiency ("FE"), is equally important because it represents how effectively the electric charge converts $CO_2$ to product instead of generating waste. All of these intrinsic failings of prior art catalysts still need to be overcome.

Thus, there remains an unmet need for $CO_2RR$ electrocatalysts and catalysts that drive reactions towards the formation of carbon monoxide, formic acid, isopropanol, glycerol, and higher order hydrocarbons from carbon dioxide.

SUMMARY

Embodiments described herein relate generally to electrocatalysts for carbon dioxide capture and conversion allowing for new routes to high energy hydrocarbon formation and high efficiency conversion of carbon dioxide. According to some embodiments, high surface area, carbonaceous nano-electrocatalysts containing a metal center from the form of single atom to size-controlled uniform metal cluster are constructed using a lithium-melt method. Herein, the metal can be main group metals, transition metals and inner transition metals. These electrocatalysts are demonstrated to be highly efficient with high selectivity and stable in promoting $CO_2$ to chemicals and fuels during electrocatalytic $CO_2RR$. Specifically, when the catalytic center changes the form from single atoms to metal clusters of different size, the electrocatalytic $CO_2RR$ leads to the formation of different chemicals with high FE. Furthermore, a very low onset voltage can be achieved, a highly sought after phenomenon in the field of $CO_2$ conversion in improving energy efficiency. Catalysts are composed of highly porous carbon supports intercalated by the transition metals.

Other embodiments described herein relate generally to electrocatalysts for carbon dioxide capture and conversion allowing for new routes to high energy hydrocarbon formation as well as high efficiency conversion of carbon dioxide. Specifically, the embodiments describes the electrocatalysts for direct conversion of $CO_2$ to glycerol. According to some embodiments, various high surface area, carbon supports have been used to prepare electro-catalysts containing Sn and Cu based transition metal centers from the form of single atom to size-controlled uniform metal cluster using an amalgamated lithium metal ("ALM") method. These electro-catalysts are demonstrated to be highly efficient with high selectivity at low overpotentials and stable in promoting $CO_2$ to glycerol during electrocatalytic $CO_2RR$. Specifically, Sn or Cu metal supported over several amorphous carbons with different surface areas and morphologies can lead to $CO_2RR$ to glycerol with high FE and low onset voltages at different combination of carbon and metal loading.

Yet further embodiments described herein relate generally to electrocatalysts for carbon dioxide capture and conversion allowing for new routes to high energy hydrocarbon formation as well as high efficiency conversion of carbon dioxide. Specifically, the embodiments describes the electrocatalysts for direct conversion of $CO_2$ to isopropanol. According to some embodiments, two high surface area, carbon supports, BP2000 and DLC Supra-50, have been used to prepare electro-catalysts containing Sn and Cu based transition metal centers from the form size-controlled uniform metal cluster using an ALM method. These electro-catalysts are demonstrated to be highly efficient with high selectivity at low overpotentials and stable in promoting $CO_2$ to isopropanol during electrocatalytic $CO_2RR$. Specifically, Sn or Cu metal supported over high surface area, high porosity amorphous carbons can lead to $CO_2RR$ to isopropanol with high FE and low onset voltages at different combination of carbon and metal loading.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein.

BRIEF DESCRIPTION OF FIGURES

The foregoing and other features of the present disclosure will become more fully apparent from the following description and appended claims, taken in conjunction with the accompanying figures. Understanding that these figures depict only several implementations in accordance with the disclosure and are therefore, not to be considered limiting of its scope, the disclosure will be described with additional specificity and detail through use of the accompanying figures.

5

Figure 18:
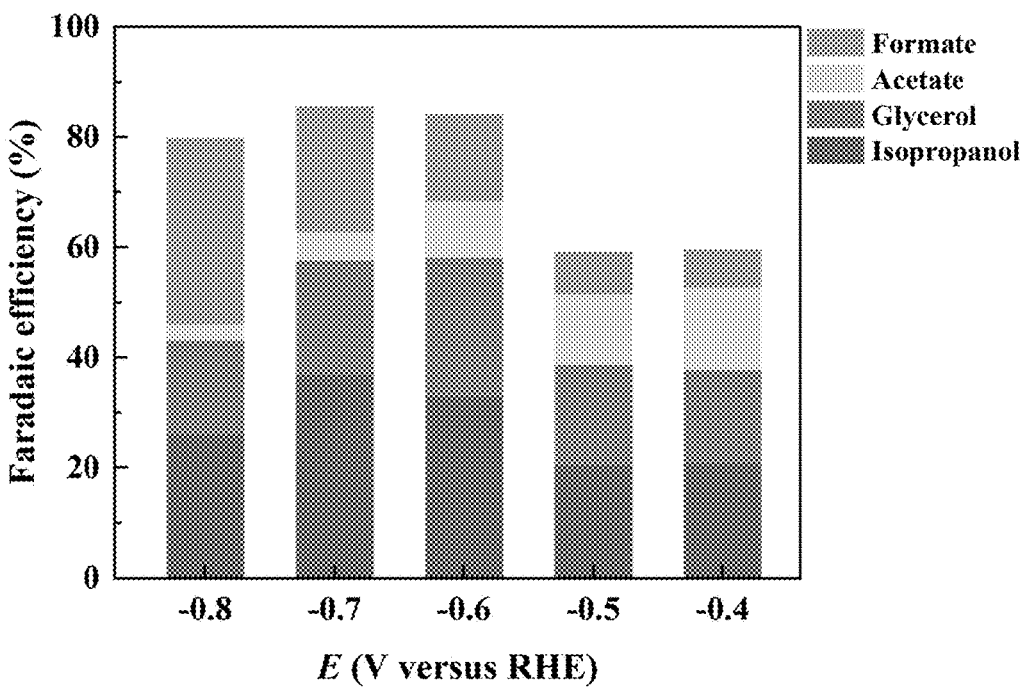

FIG. 18 shows FEs and the product distribution at different cell potential of CO$_2$RR electrocatalysis over the catalyst of 20% Sn over carbon support BP2000 (Sn/BP2000-20), according to Example 18.

Figure 19:
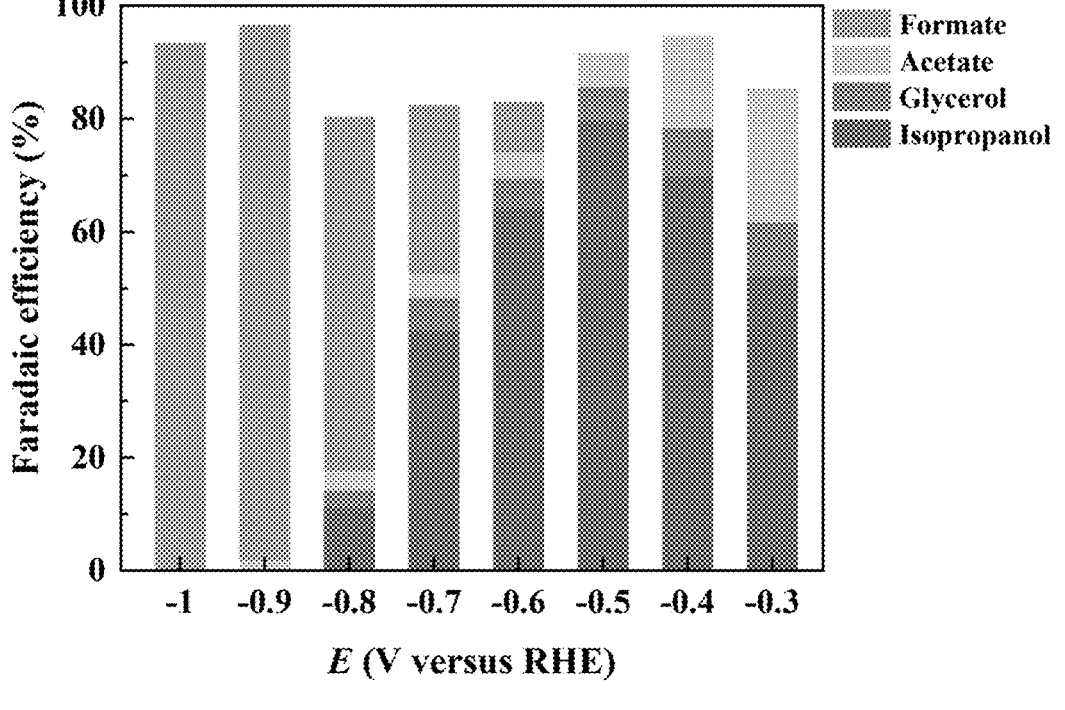
Figure 20:
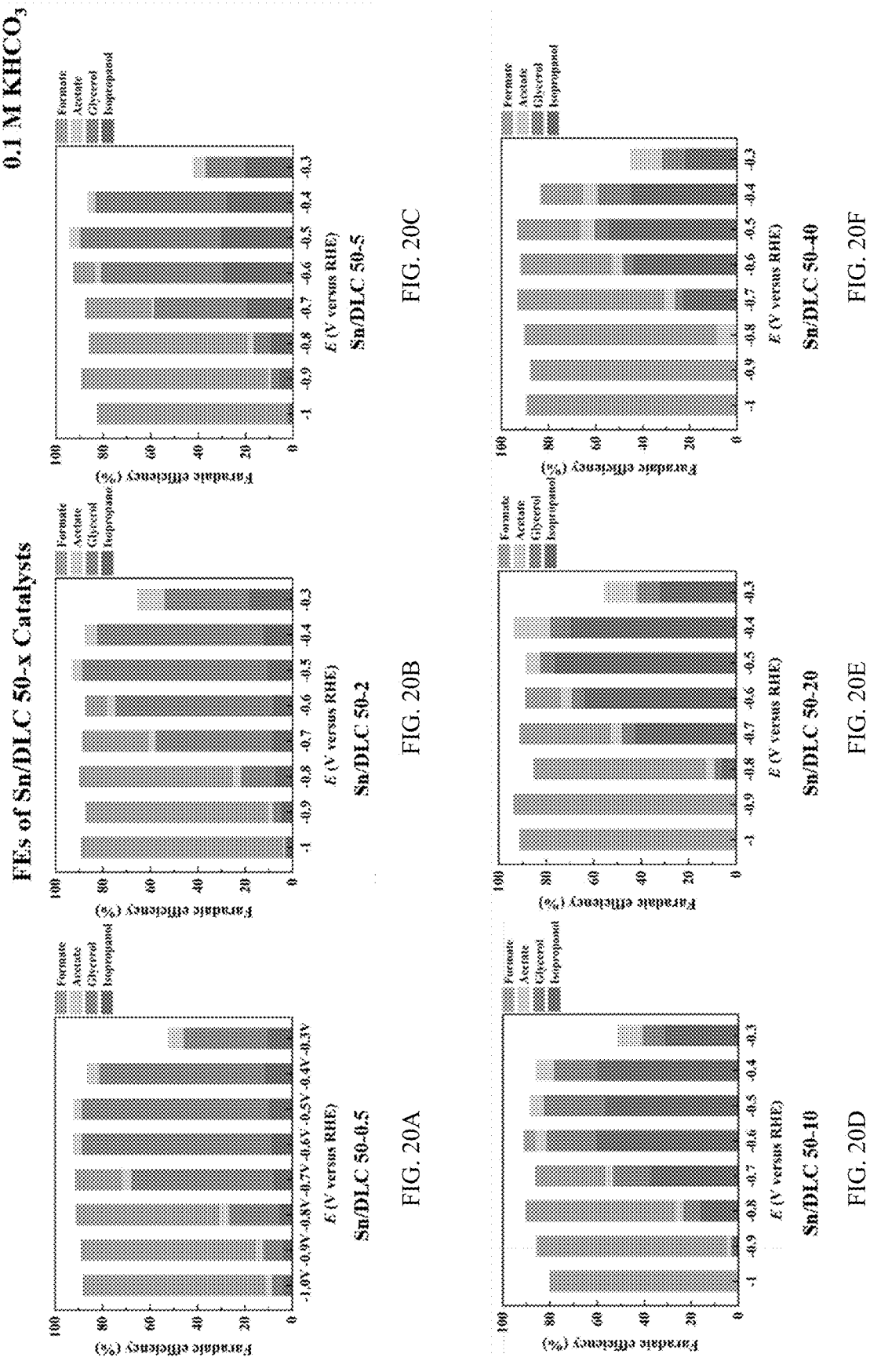

FIG. 19 shows FEs and the product distribution at different cell potential of CO$_2$RR electrocatalysis over the catalyst of 20% Sn over carbon support DLC Supra (Sn/DLC Supra-20), according to Example 19.

FIGS. 20A-20F show FEs and the product distributions at different cell potential of CO$_2$RR electrocatalysis over the catalyst Sn of various loading X % over carbon support DLC Supra (Sn/DLC Supra-X): Sn/DLC 50-0.5 (FIG. 20A), Sn/DLC 50-2 (FIG. 20B), Sn/DLC 50-5 (FIG. 20C), Sn/DLC 50-10 (FIG. 20D), Sn/DLC 50-20 (FIG. 20E), and Sn/DLC 50-40 (FIG. 20F), according to Example 20.

Figure 21:
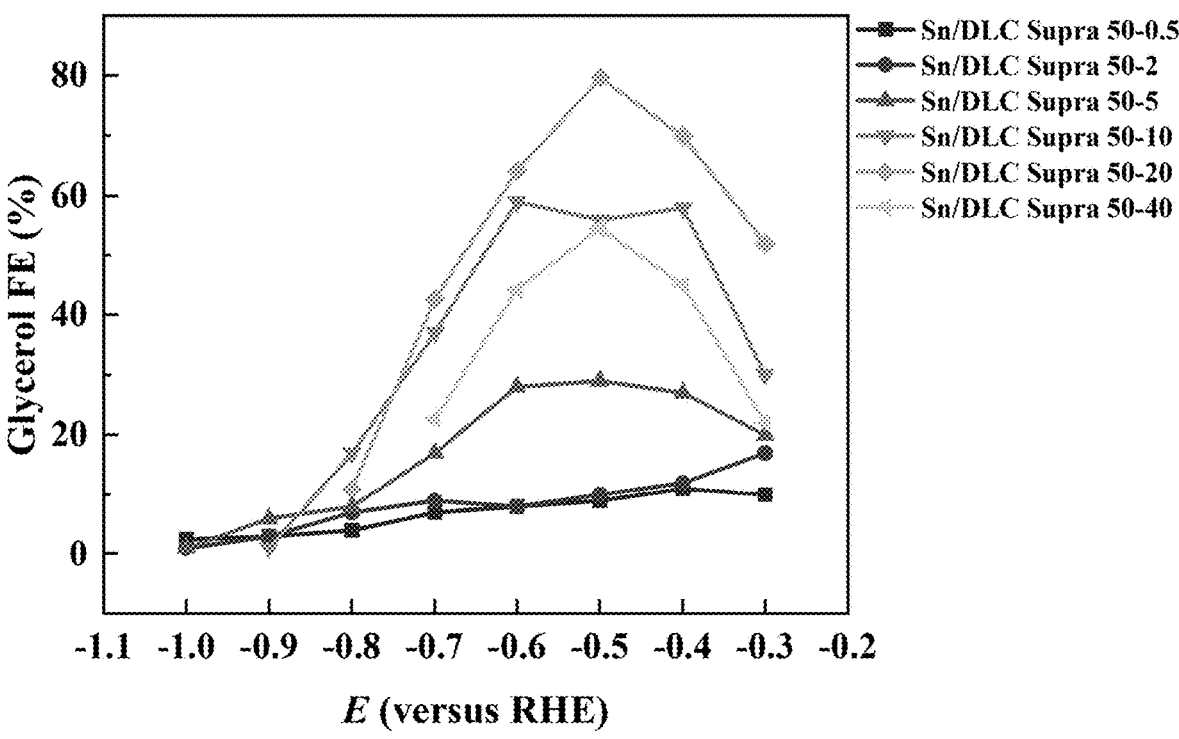

FIG. 21 shows FEs as the function of cell potential measured over Sn/DLC Supra catalysts with different Sn loadings, according to Example 21.

Figure 22:

FIG. 22 shows a graph of pore widths for tested carbon supports.

Reference is made to the accompanying figures throughout the following detailed description. In the figures, similar symbols typically identify similar components, unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

DETAILED DESCRIPTION OF VARIOUS EMBODIMENTS

Embodiments described herein relate generally to carbon supported carbon dioxide reduction electrocatalysts. Specific embodiments relate to the utilization of lithium melt synthesis for the formation of carbon supported single atom electrocatalysts. In further embodiments, carbon supported single atom electrocatalysts are used as catalysts for carbon dioxide reduction reactions ("CO$_2$RR"), and, for example, towards the formation of acetate, glycerol, isopropanol, ethanol, and formate. The catalysts according to some embodiments exhibit excellent selectivity, efficiency and durability for converting carbon dioxide towards selective production of high order hydrocarbons under very low overpotentials.

Described herein in one embodiment are a new class of CO$_2$RR electrocatalysts derived from bulk tin and bismuth over high surface area carbonaceous support. According to one embodiment, the electrocatalysts are active even for low temperature aqueous application. The low temperature refers to the range from 0° C. to less than 100° C. Depending on the metal loading, these catalysts have compositions of stable and highly dispersed single atom of a metal ("M"), where M may be transition metals, inner transition metals and main group metal, such as the metals identified in FIG. 11 (e.g., Sn, In or Bi, or metal particle of Sn, In, or Bi with uniform size decorated inside of carbonaceous material). The metal loading range under which the metal remains in the form of single atom depends on the surface area of the support.

Generally speaking, the higher the surface area of the support, the higher the loading of the metal can be while maintaining the single atom dispersion. Loading range is fundamentally related to the surface area of the support, which is typically described as (x) m$^2$/g, When certain molar amount of catalytic metal atoms (y) with atomic mass of (w) is loaded on the support, the average distance between the atoms can be calculated, assuming they are uniformly distributed. Thus, in one embodiment, the loading range is a combination of x, y, and w, as yw/x.

For example, for amorphous carbon support of XC72 material, which has the specific surface area at ~200 m$^2$/g, the loading ranges associated with the tin catalytic sites remaining "single atom" is 0.05-3.2 wt %. At loading from 3.2-55 wt %, the tin remains in particle form of different size.

Figure 11:
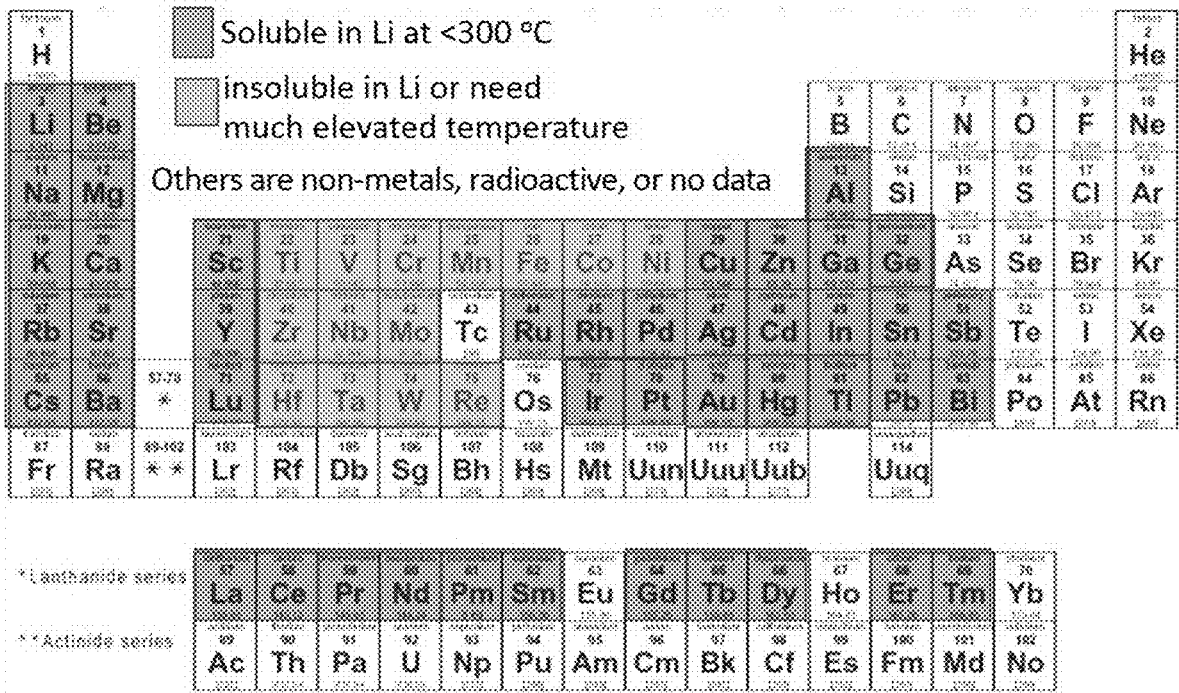
FIG. 11 shows the periodic table in which the metal elements shaded in red can be dissolved in molten lithium directly at temperature lower than 300° C. The metal shaded in blue can be dissolved in molten lithium only in the form of oxide, or at the temperature significantly higher than 300° C.

The amalgamated Li-M method can also be applied to a wide variety of metals, such as those identified in FIG. 11 as soluble in molten lithium under 300° C. Some catalysis metals, such as those identified in FIG. 11 (e.g., Fe, Ni, Co), cannot be dissolved directly by molten lithium. However, in one embodiment, tor the metals that cannot be dissolved by molten lithium in their own metal form, such metals can be dissolved in molten lithium in their metal oxide forms. During the dissolution process, a metal oxide will react with molten lithium, which is a strong reducing agent by itself through the reaction $2Li+M_xO \rightarrow Li_2O+xM$. The use of metal oxide shares similar fundamental principles and could in principle cover the metals that are not shaded in the periodic table of FIG. 11. This pathway has been demonstrated with a wide variety of metal oxides, such as NiO, Co$_3$O$_4$, TiO$_2$, V$_2$O$_5$, MoO$_3$ and Fe$_2$O$_3$. Depending on the initial size of the metal oxide particles, the resulting metal can be single atoms or clusters or nanoparticles.

In one embodiment, CO$_2$RR electrocatalysts are prepared in the following steps: (1) dissolving bulk metal M or a bulk metal oxide (as indicated in FIG. 11) in a melt lithium; (2) quickly quenching the lithium melt to room temperature to form lithium-M ("Li-M") amalgam; (3) converting the Li-M amalgam to lithium hydroxide ("LiOH") powder embedded with uniformly dispersed M; (4) mixing LiOH-M powder with carbon support; and (5) leaching away LiOH through water rinsing to form the final catalyst of M supported by carbon ("M/C").

In the first step, a selected metal (e.g., tin (Sn), bismuth (Bi), indium (In), copper (Cu), silver (Ag), rhodium (Rh), or any metal active for CO$_2$RR and dissolvable in molten alkaline metal, or some combination thereof) is dissolved. The type of the metal used as well as its loading in the catalyst can affect the CO$_2$RR conversion product output, FE, and onset potential. For example, in the case of Sn, when Sn loading on substrates is less than 0.8 wt %, the conversion product is predominantly acetate with the FE as high as 90%. With a further increase of the Sn loading from 0.8-6.4 wt %, the conversion product is predominantly ethanol, and a FE as high as 92% can be reached. By continuously increasing Sn loading higher than 6.4 wt %, the conversion product becomes predominantly of formate with FE as high as 90% can be reached.

Another example is In/C catalyst. When the In loading on substrates is in the range of 0-3.2 wt %, high FE of 90% for conversion to formate can be found. In particular, the metal can be formed directly from bulk metal (e.g., in the form of ingot, wire, powder, shredded pieces) in the alkaline metal melt rather than the conventional wet chemistry synthesis methods involving dissolving metal salt or metal complex in aqueous or organic solution, following multi-step impregnation, drying, reduction, etc. Alternatively, the metal in the catalyst can be formed from its oxide, which can be dissolved in lithium through reducing reaction.

In one embodiment, alkaline metals (e.g., lithium (Li), sodium (Na), potassium (K)) are used as the molten media to dissolve the aforementioned metals to form a solid solution. In a preferred embodiment, Li is used as the molten medium because it can dissolve most of the metals based on the lithium-metal phase diagrams. In one embodiment, the synthesis proceeds through the dispersion of transition metal into a hot lithium solution under inert atmosphere, which the temperature for molten Li is in the range from 183-1330° C., which covers the temperature range between the melting and boiling points of Li. For other alkaline metals, the molten temperature range is between their respective melting and boiling points. The molten lithium temperature used for dissolving a particular metal is based on the phase diagram, which is distinctive for each metal. The Li-to-metal ratio and temperature should resort to that specific phase diagram. The molten lithium temperature used for dissolving a particular metal is based on the phase diagram, with the temperature generally within the range of 183~1330° C. The ratio of metal (or metal oxide) to lithium melt is considered along with temperature in the context of the associated phase diagram since each Li-Metal phase diagram is distinctive. The metals shaded in red in FIG. 11 can be dissolved into molten Li under 300° C., while the metals shaded in blue in FIG. 2 can be dissolved into molten Li above 300° C., in the range of 300~500° C. In a preferred embodiment, the elements shaded in blue should be used in their metal oxide form, which can be reduced to metal single atoms or metal clusters or metal nanoparticles by molten Li at the temperature lower than 300° C. The metal-to-lithium ratio will impact the final format of the metals on the support. In a preferred embodiment, the molar ratio of metal to Li is 1:5000~1:400 in order to keep the metal atomically dispersed or in very small cluster size, such as approximately 5 nm spacing.

The molten alkaline metal with added transition metal may be maintained at a temperature, such as 180-1330° C., for a period of time, such as up to 4 hours, to allow formation of the Li-M amalgam. In one embodiment, the liquid melt is mixed, such as by sonication or mechanical interaction. The mixing creates a single atom or metal cluster dispersion within the liquid lithium, depending the amount of M added. The synthesis proceeds through the dispersion of transition metal within a lithium melt under inert atmosphere conditions without contamination by other elements.

In the second step, the Li melt is rapidly quenched to ambient temperature (20-22° C.) to form a Li-M amalgam. During this step, metal M is "frozen" in the form of single atom or metal cluster dispersion within the solid Li. As used here, "quench" refers the means to rapid cooling of the molten lithium so that it can be solidified to solid lithium metal while maintaining the state of metal M in the lithium. For example, in one embodiment the quenching is from 1-60 seconds, such as 5-30 seconds. The quenching may be done by rapidly pouring the melt onto a heat-dissipating surface, such as a clean stainless-steel plate, to quench the melt and avoid aggregation of metal components. In one embodiment, the molten material is cooled in less than 1 minute, such as about 30 seconds.

In the third step, the amalgamate Li-M is exposed to moist air to convert Li metal to LiOH forming a lithium hydroxide-M ("LiOH-M") mixture. In one embodiment, the moist air has a relative humidity ("RH") range of 20-100% (e.g., ambient humidity), a pressure range of 0.1-10 atmospheres (e.g., ambient pressure), and a temperature range of 5-50° C. (e.g., room temperature). In one embodiment, ambient temperature and humidity are utilized. If the humidity is low (<10%), the conversion takes longer; for example, at less than 10% humidity, it takes up to 3 days to convert the sample. The lithium-metal solid may be cut into smaller pieces in order to increase the reaction surface area.

In an example embodiment, the moist air has a relative humidity range of 60~100 RH %, at 1 atmosphere pressure, and at room temperature. During the process, M remains in the form of single atom or metal cluster/particle dispersion within the solid matrix of LiOH; the conversion to LiOH, in one embodiment, does not alter the form as single atom or metal cluster/particle. In one embodiment, the Li-M amalgam is cut into small pieces to facilitate the interaction with moisture and oxygen for conversion to LiOH. In other embodiments, other mechanical methods that can break down solid solutions into finer pieces to facilitate the interaction with moisture and air may be used. The Li-M amalgam pieces obtained after the reduction in size will be exposed to humidified air so that all of the lithium can be converted to lithium oxide ("Li$_2$O") and LiOH. It should be understood that for other alkaline metals, the same basic physical processing can be done to facilitate formation of the respective alkaline metal oxide. During such processes, Li metal will first be oxidized by the oxygen in air to form Li$_2$O, which subsequently reacts with moisture ("H$_2$O") to form LiOH. In a preferred embodiment, the moist air should have relative humidity of 50-100%.

In the fourth step, the LiOH-M mixture, either in the form single atom or metal cluster/particle, is thoroughly mixed with carbonaceous support. The mixing process maybe manual or automated, for example mortar and pestal may require 1~2 hours. The mixing may be by sonication or mechanical interaction such as ball milling. If ball milling is used, one embodiment mixes for 5 minutes per run and 2 minutes interval, for a total of 5 runs.

In the fifth step, the LiOH-M mixture is rinsed with water to wash away soluble LiOH while keeping M over the carbon substrate as the final catalyst. During the leaching step, the water dissolves LiOH to form a concentrated alkaline solution, which subsequently oxidize the carbon surface to form surface functional groups (e.g., —OH, —COOH, —CO groups), promoting the binding of M and M cluster in the new catalyst. In one embodiment, the water is slowly and drop-wisely added to the mixture, keeping the mixture appearing as a slurry to avoid the LiOH is completely dissolved in short period of time, which may wash off the M single atoms or cluster due to the rigorous flow of liquid.

As described herein, the mixing of LiOH-M mixture is with a carbonaceous support. The carbonaceous support has a porous structure, such as having a surface area of 200-1200 m$^2$/g or higher. In one embodiment, the carbonaceous support can either be a commercial support (e.g., Vulcan XC-72™ or Ketjen Black™) or one synthesized based on high surface area materials (e.g., carbon-derived from high surface precursors such as zeolites, metal-organic frameworks, or other similar materials). Metal loading on supports are related to the surface area of the support, which is typically described as Brunauer-Emmett-Teller ("BET") surface area as (x) m$^2$/g. The higher BET surface area, the more metal loading can be added while maintaining the average distance between the metal atoms. While there is no required size range of pores, typically, the BET surface area of the support is higher than 200 m$^2$/g. The carbonaceous support coupling forms a carbonaceous electrocatalyst with high specific surface area and high porosity with micropore fraction, uniformly decorated by the transition metal single atoms or crystallites reduced and agglomerated from the transition metal. As used herein, "uniformly decorated" refers to uniformly distributed single atoms or metal clusters/particles present throughout the carbonaceous material from the outside to the inside of the porous material.

In other embodiments, M is a multi-metallic. In one embodiment, such multi-metallic catalysts are formed by modifying a monometallic system through partial replacement of an initial transition metal with a second transition metal during the first part of lithium dispersion. Such replacement can be applied during the initial lithium melt step. Examples include interchanging a fraction of Sn, In or Bi with Cu, Ag, or Rh to form bimetallic $CO_2RR$ catalysts, such as Sn/In, Sn/Bi, Sn/Cu, Sn/Ag, Sn/Bi, Sn/Rh, In/Bi, In/Cu, In/Ag, In/Rh, Bi/Cu, Bi/Ag, Bi/Rh, etc. The result is Li-M1-M2, where M1 is first metal and M2 is second metal, or Li-multi-metals melt, which can then be processed as described above with a humidity exposure to convert the Li to LiOH and then mixing with a carbonaceous support.

In one embodiment, the washed catalyst mixture is then dried under vacuum oven to remove the moisture at 50-100° C. After such process, the atomically dispersed metal is then transferred over a conductive carbon surface for an electrochemical reaction while remaining highly segregated.

In a further embodiment, catalysts can be made into inks for further processing applications such as preparation of membrane electrode assembly. $CO_2RR$ catalysts described herein have the following advantages: (1) active and stable in aqueous media; (2) high selectivity with FE achievable by controlling electrochemical potential; (3) easy application to surfaces as well as thin films or on substrates; and (4) use of low cost, earth abundant transition metal materials. Unlike the prior art of preparing $CO_2$ catalysts, nitrogen-containing carbon supports are not required to prepare $CO_2RR$ catalysts. Thus, one embodiment relates to a nitrogen-free carbon support or nitrogen-free organic solution process. In the prior art, nitrogen-containing carbon is needed as support because that the nitrogen embedded in the carbon serves as ligation functional group to anchor a metal M. Not limited by hypothesis, M is anchored by oxidized carbon surface functional group such as OH, COOH, and CO, etc. in the described embodiments herein. Furthermore, the transfer of catalytic center containing M to the support is carried out at room temperature. Conventional high temperature activation as well as expensive chemical processing post metal dispersion is no longer necessary.

Overcoming low product selectivity and low FE of the existing electrocatalysts is a major challenge and is accomplished for embodiments described herein, the described $CO_2RR$ electrocatalysts, according to one embodiment, show high selectivity towards single product formation as well as high FE. Furthermore, the $CO_2RR$ conversion selectivity, dominating product and onset potential can be altered by changing the metal loading therefore the metal dispersion from single atom to metal cluster. When the metal loading is low (<3.2 wt %) or it is in single atom dispersion form, the FE of products (ethanol, acetate et al) can reach as high as 90%, and the onset potential can reach as low as –0.3V for ethanol and –0.4V for acetate. When the metal loading is high (>6.4 wt %) or it is in nanoparticle form, the FE of products (ethanol, acetate et al) can drop below 40%. For example, the FE approaches >90% at low onset potential of 0.6V was observed over the Sn/C catalyst containing 0.2 wt % Sn. At this loading, Sn is mainly in atomically dispersed form. When the Sn loading is increased to 3.2 wt %, ethanol becomes the dominant $CO_2RR$ production with FE>90% at low polarization potential of 0.5 V and small Sn crystallite is observed. A further increase of Sn loading to >51 wt % leads to dominate conversion product of formate with FE>90% and onset potential as low as 0.3 V. At this loading Sn is in the form of large crystallites. Another important benefit of the electrocatalyst, according one embodiment, is to control the product formation by simply adjusting the amount of M applied to the carbon support.

In one embodiment the catalyst comprises In, such as wherein the catalyst has 0.1-55 wt % of In. In one embodiment, the In catalyst has a Faradaic efficiency of at least 90% in converting of carbon dioxide to formate at –0.6 V (RHE).

In one embodiment the catalyst comprises Bi, such as wherein the catalyst has 0.1-55 wt % of Bi, such as 0.2-50 wt %. In one embodiment, the Bi catalyst has a Faradaic efficiency of at least 90% in converting of carbon dioxide to formate.

In one embodiment the catalyst comprises Sn, such as wherein the catalyst has 0.1-55 wt % of Sn. In one embodiment, the Sn catalyst has a Faradaic efficiency of at least 90% in converting of carbon dioxide to acetic acid at –0.6 V (RHE). In one embodiment the Sn catalyst has a Faradaic efficiency of at least 90% in converting of carbon dioxide to ethanol at 0.5 V (RHE).

Unlike many prior art $CO_2RR$ catalyst synthesis, which use electroplating or metal inorganic and organic based precursor chemistry, the catalyst derived from the embodiments described herein uses Li-melt solution chemistry synthesis and therefore can be easily scaled-up. In addition to the advantage of producing single atom supported over the high surface carbon, embodiments described herein can also generate catalysts containing micro-crystallites with uniform size in the dimension of nanometers by simply increasing the metal loading during amalgamated lithium-metal preparation. This allows for easy application to porous substrates or electrode surfaces without the need for advanced processing techniques.

Another embodiment of the current invention is to control the $CO_2RR$ conversion product by changing the operating potential, as will be demonstrated by the examples given below.

Electrocatalysts prepared as described herein have several advantages over that of prior art, including: (1) high FE, (2) high selectivity for desired chemical species, (3) high aqueous stability, and (4) controllable product output by controlling operating potential as well as metal loading. Electrocatalysts in accordance with embodiments herein also exhibit high stability in aqueous media and under high overpotentials. The high surface area carbon support allows for increased stability, as carbon does not easily degrade at low overpotentials. The high surface area also allows for segregation of metal single atoms and nano-particles, leading to continuous and reliable FE as well as product selectivity.

The process of preparing lithium-melt catalysts used as electrocatalysts according to some embodiments can be further elucidated by the following examples.

Figure 1:
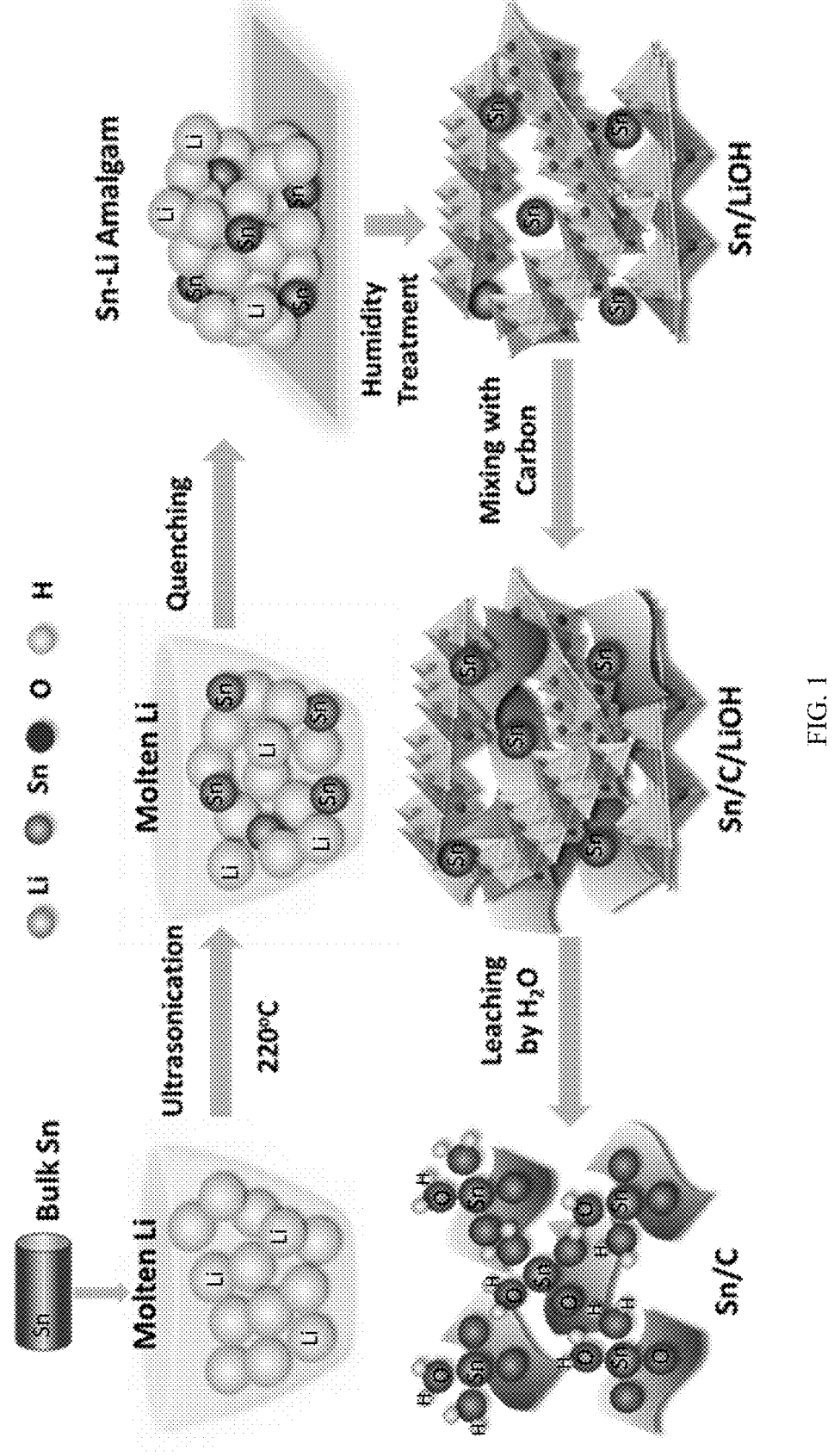
FIG. 1 shows schematics of preparing $CO_2RR$ catalyst using a lithium-metal amalgam approach, according to one embodiment.

Example 1. A schematic presentation of an example Li-melt-based electrocatalyst for $CO_2RR$ is shown in FIG. 1. Synthesis of single atoms/clusters was carried out in an inert atmosphere glovebox. Using a crucible, Li was heated to above its melting point of 180.5° C. and kept below its boiling point of 1330° C., to which a relative amount of Sn was added. An ultrasonic homogenizer was used to ensure a uniform dispersion of metal single atoms/clusters while the Li melt was maintained for 1-3 hours. Formation of a solid solution was achieved by rapidly pouring the melt onto a clean stainless steel plate to quench the melt and avoid aggregation of metal components. Once the Li—Sn melt solid cooled, the solution was removed from the glovebox, cut into small pieces, and slowly converted from Li to LiOH using humidified air. The ensuing Sn single atoms/clusters/LiOH materials were combined with the desired amount of carbon support and mixed with a mortar and pestle until homogeneous. The LiOH was leached out with copious amounts of double-distilled water, leaving the Sn single atoms/clusters embedded in the amorphous carbon support. The resulting powder was collected and used to make an ink.

The activity of the catalyst was evaluated by rotating disk electrode ("RDE") method in the $CO_2$-purged acidic bicarbonate solution electrolyte. The activity of catalysts was measured through cyclic voltammetry and compared to prior art. The chemicals generated in the liquid phase were collected. The product composition and FE were evaluated using a combination of nuclear magnetic resonance ("NMR").

Example 2. A Sn/C $CO_2$RR catalyst was synthesized according to the steps described in Example 1. Specifically, 0.29 mol of Li (99.9% Sigma-Aldrich) was added into a Ni crucible and heated to 220° C. to form molten Li. Then, 0.042 mmol (~5 mg) of Sn foil (99.9% Alfa-Aesar) were added into the molten Li. An ultrasonic homogenizer was used to ensure a homogeneous dispersion of the bulk Sn foil into single atoms and prevent them from precipitation and re-aggregation in the molten Li while the molten Li was maintained at 220° C. for 2 hours. The melted metals were then quickly poured onto a clean 316-stainless steel plates to quench to solid solution. After cooling, the Sn—Li amalgam was taken out from the glovebox in ambience and cut into small pieces, which were then slowly converted from Li to LiOH under humidified air at ambient temperature. The obtained Sn in LiOH powder was homogeneously mixed with 2.5 g carbon black support by grinding the mixture with an agate mortar and pestle. The resulting mixture was filtered with copious amount of de-ionized water to leach off LiOH. Finally, the filtered carbon-Sn mixture was dried under vacuum at 60° C. for 24 hours to form 0.2 wt % Sn over carbon ("Sn/C"), named "Sn/C-0.2."

A catalyst ink was prepared by adding 5 mg Sn/C-0.2 to a solution of 50 mg Nafion® and 200 mg methanol. The resulting solution was sonicated for 60 minutes to ensure full dispersion of the electrocatalyst. About 20 μL of the solution was applied to a glassy carbon RDE with a surface area of 0.196 cm² in droplets. The catalyst was tested at RDE rotation rate of 1600 rpm in $CO_2$ saturated bicarbonate solution (pH 6.8). Chronoamperometry was employed at −0.4V to −1.3V at 0.1V intervals to test the catalyst stability while collecting converted hydrocarbons using NMR analysis.

Figure 2:
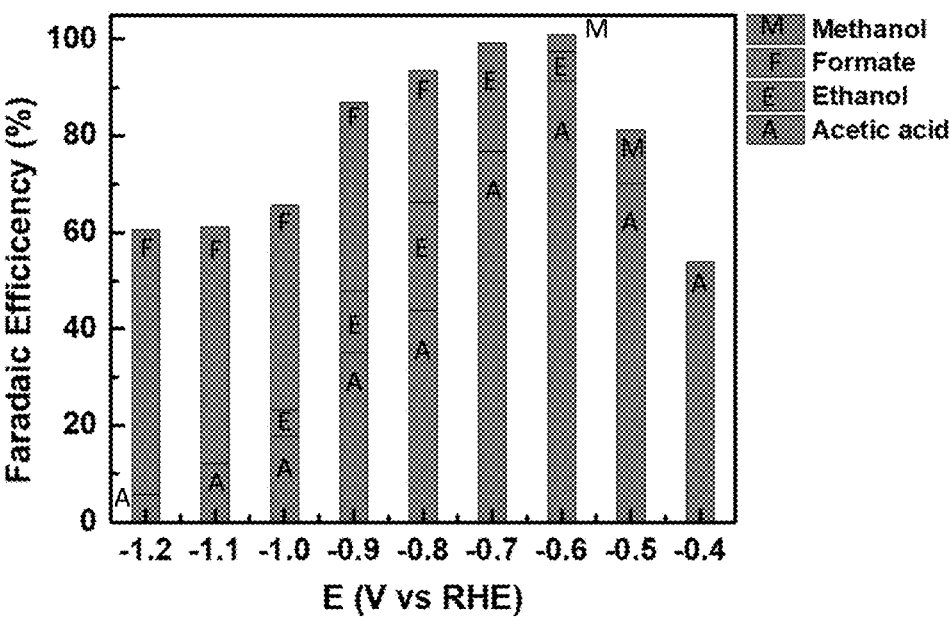
FIG. 2 shows FE and the product distribution at different polarization potentials of $CO_2RR$ electrocatalysis over catalyst Sn/C-0.2, according to Example 2.

The FE of $CO_2$RR was calculated according to the Equation 1:

$$FE_i = \frac{Q_i}{Q_{total}} \qquad (1)$$

where i represents different products (e.g., acetate, ethanol, and formate) and $Q_i$ and $Q_{total}$ represent the number of charges transferred to the product and the total number of charges passed into the solution, respectively. FIG. 2 shows the FE and the different product distribution at various polarization potentials of $CO_2$RR electrocatalysis over the catalyst Sn/C-0.2. As can be seen, the catalyst achieved higher than 90% FE for converting $CO_2$ to acetic acid at 0.6 V (RHE).

Figure 3:
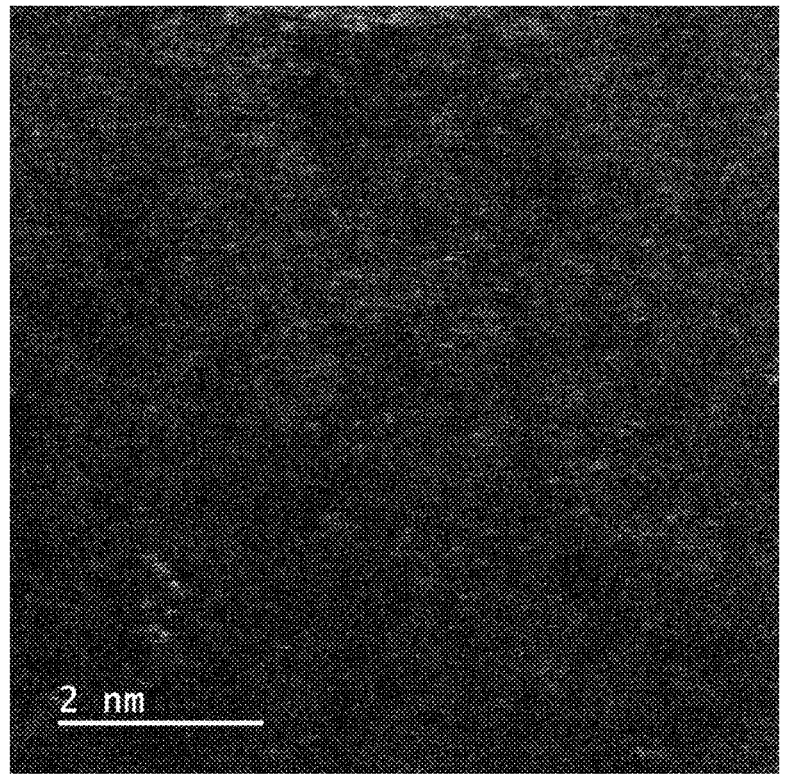
FIG. 3 is a representative high-angle annular dark-field scanning transmission electron microscopy ("HAADF-STEM") image of Sn/C-0.2 showing the presence of isolated tin (Sn) species with white dot in the image, according to Example 2.

Example 3. The catalyst Sn/C-0.2 synthesized according to Example 2 was investigated by HAADF-STEM. FIG. 3 shows that tin in the catalyst was predominately present as single atoms, according to the HAADF-STEM image.

Figure 4:
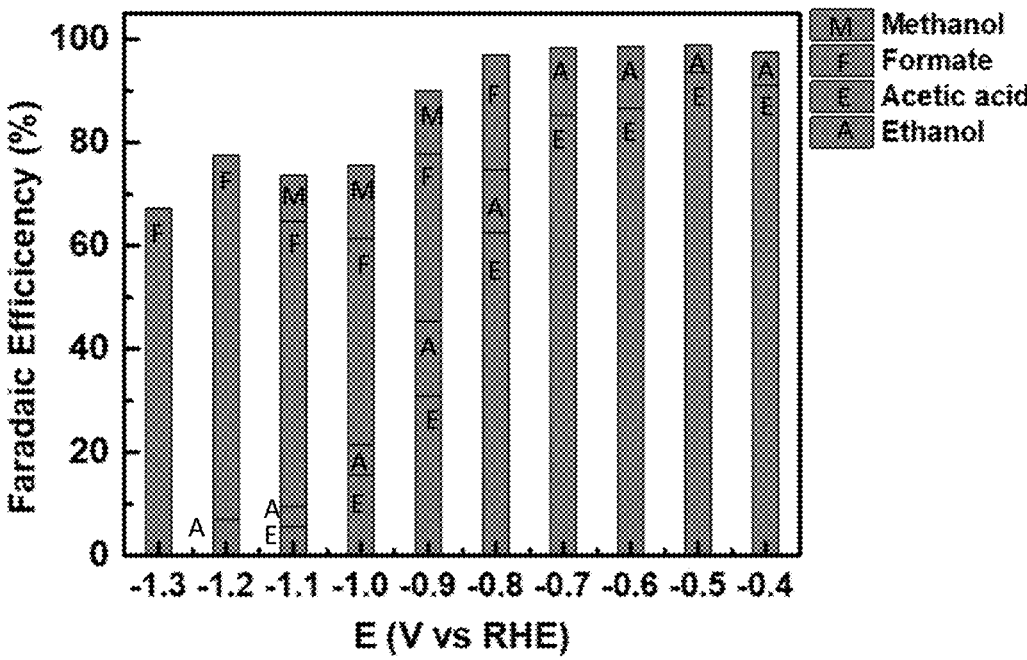
FIG. 4 shows FE and the product distribution at different polarization potentials of $CO_2RR$ electrocatalysis over catalyst Sn/C-3.2, according to Example 4.

Example 4. A Sn/C $CO_2$RR catalyst was synthesized according to the steps described in Examples 1 and 2 except that 0.674 mmol (~80 mg) of Sn foil (99.9% Alfa-Aesar) was added to the 0.29 mol of molten Li. The final catalyst has 3.2 wt % Sn/C, named "Sn/C-3.2." FIG. 4 shows the FE and the different product distribution at various polarization potentials of $CO_2$RR electrocatalysis over the catalyst Sn/C-3.2. As can be seen, the catalyst achieved higher than 90% FE for converting $CO_2$ to ethanol at 0.5V (RHE).

Figure 5:
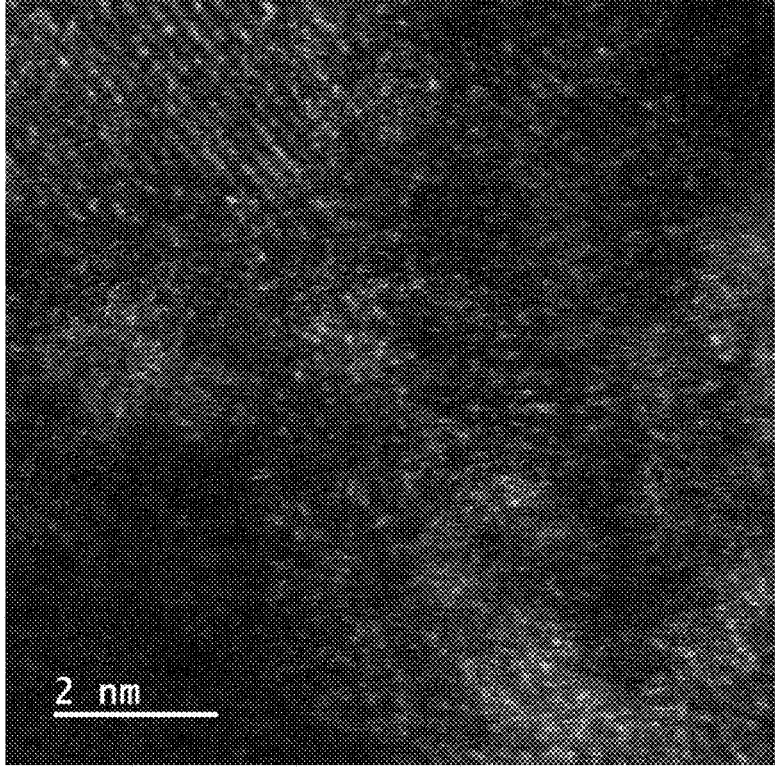
FIG. 5 is a representative HAADF-STEM image of Sn/C-3.2 showing the presence of isolated Sn species with white dot in the image.

Example 5. The catalyst Sn/C-3.2 synthesized according to Example 4 was investigated by HAADF-STEM. FIG. 5 shows that Sn in the catalyst was present as single atoms with closer interatomic distance than that found in Example 3, according to the HAADF-STEM image.

Figure 6:
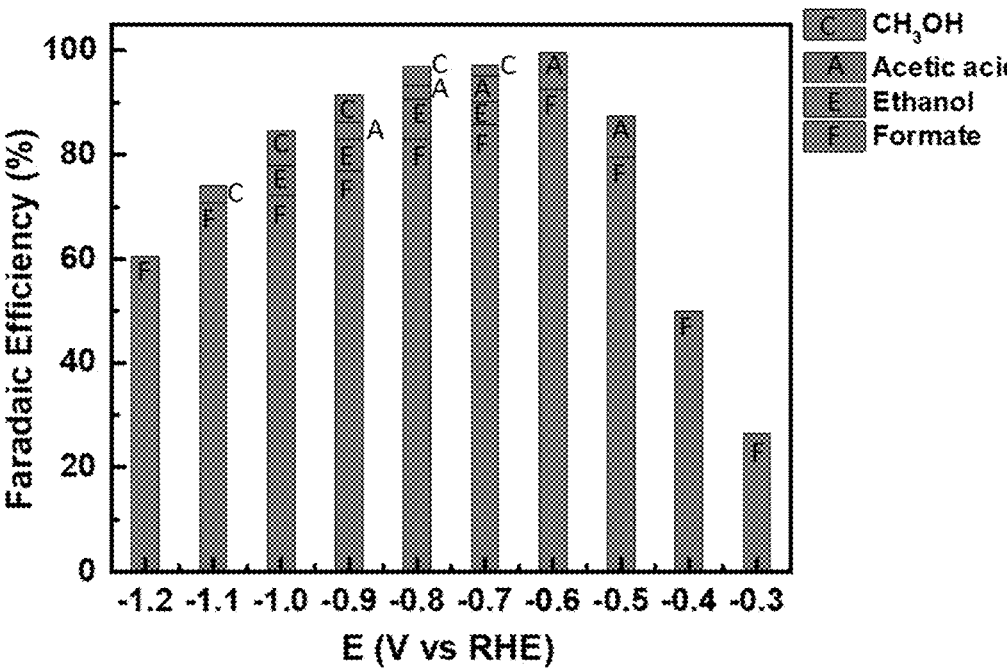
FIG. 6 shows FE and the product distribution at different polarization potentials of $CO_2RR$ electrocatalysis over catalyst Sn/C-51.2, according to Example 6.

Example 6. A Sn/C $CO_2$RR catalyst was synthesized according to the steps described in Examples 1 and 2 except that 10.8 mmol (~1.28 g) of Sn foil (99.9% Alfa-Aesar) was added into the 0.29 mol of molten Li. The final catalyst has 51.2 wt % Sn/C, named "Sn/C-51.2." FIG. 6 shows the FE and the different product distribution at various polarization potentials of $CO_2$RR electrocatalysis over the catalyst Sn/C-51.2. As can be seen, the catalyst achieved higher than 90% FE for converting $CO_2$ to formate at 0.6 V (RHE).

Figure 7:
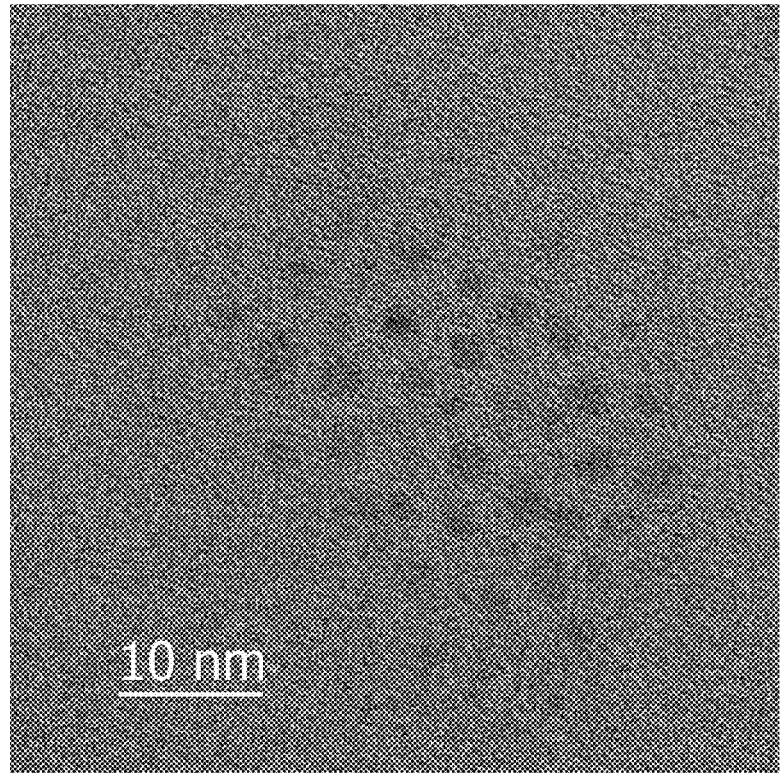
FIG. 7 is a representative HAADF-STEM image of Sn/C-51.2 showing the presence of isolated Sn nanoparticles with the particle size of 5 nm.

Example 7. The catalyst Sn/C-3.2 synthesized according to Example 4 was investigated by HAADF-STEM. FIG. 7 shows that Sn in the catalyst was present as uniformly distributed Sn particle with average particle size of 5 nm, according to HAADF-STEM image.

Figure 8:
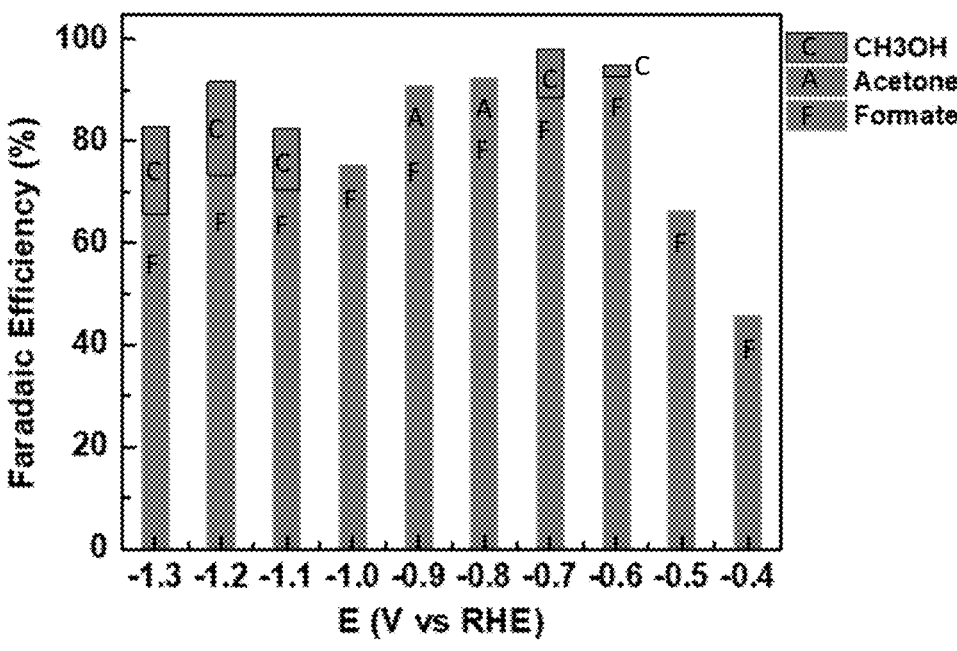
FIG. 8 shows FE and the product distribution at different polarization potentials of $CO_2RR$ electrocatalysis over catalyst In/C-0.2, according to Example 8.

Example 8. A carbon-supported In $CO_2$RR catalyst, named "In/C-0.2," was synthesized according to the procedure described in Examples 1 and 2. Briefly, 0.044 mmol (~5 mg) of In foil (99.9% Alfa-Aesar) was added into the 0.29 mol of molten Li. The final catalyst has 0.2 wt % In over carbon ("In/C"). FIG. 8 shows the FE and the different product distribution at various polarization potentials of $CO_2$RR electrocatalysis over the catalyst In/C-0.2. As can be seen, the catalyst achieved higher than 90% FE for converting $CO_2$ to formate at −0.6 V and −0.7 V (RHE).

Figure 9:
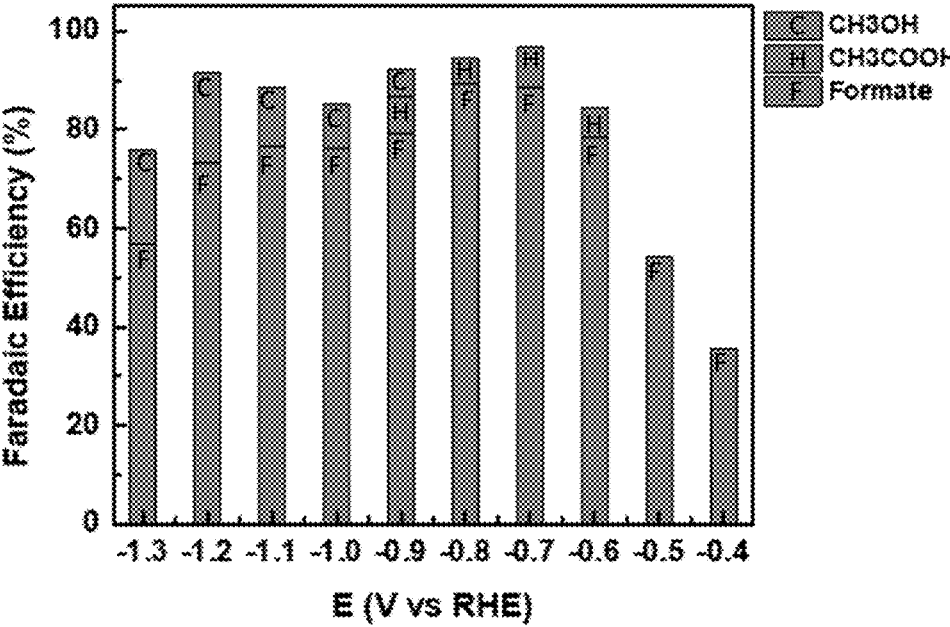
FIG. 9 shows FE and the product distribution at different polarization potentials of $CO_2RR$ electrocatalysis over catalyst In/C-0.8, according to Example 9.

Example 9. A carbon-supported In $CO_2$RR catalyst, named "In/C-0.8," was synthesized according to the procedure described in Examples 1 and 2. Briefly, 0.174 mmol (~20 mg) of In foil (99.9% Alfa-Aesar) was added into the 0.29 mol of molten Li. The final catalyst has 0.8 wt % In/C. FIG. 9 shows the FE and the different product distribution at various polarization potentials of $CO_2$RR electrocatalysis over the catalyst In/C-0.8. As can be seen, the catalyst achieved higher than 90% FE for converting $CO_2$ to formate at −0.7 V (RHE).

Figure 10:
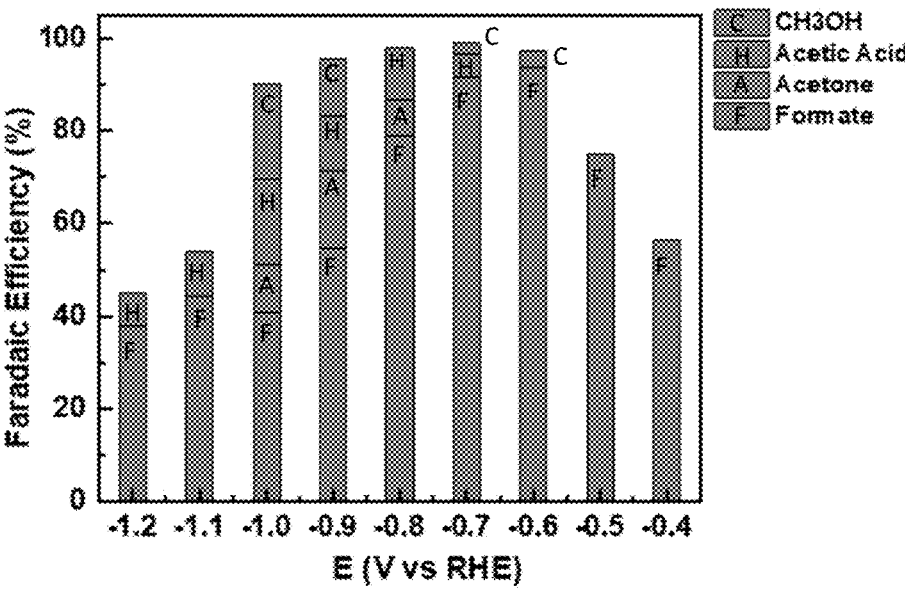
FIG. 10 shows FE and the product distribution at different polarization potentials of $CO_2RR$ electrocatalysis over catalyst In/C-3.2, according to Example 10.

Example 10. A carbon supported indium $CO_2$RR catalyst, named "In/C-3.2," was synthesized according to the procedure described in Examples 1 and 2. Briefly, 0.697 mmol (~80 mg) of In foil (99.9% Alfa-Aesar) was added into the 0.29 mol of molten Li. The final catalyst has 3.2 wt % In/C. FIG. 10 shows the FE and the different product distribution at various polarization potentials of $CO_2$RR electrocatalysis over the catalyst In/C-3.2. As can be seen, the catalyst achieved higher than 90% FE for converting $CO_2$ to formate at −0.6 V and −0.7 V (RHE).

Glycerol Production.

In one embodiment, the embodiments describes the electrocatalysts for direct conversion of $CO_2$ to glycerol. These embodiments relate to a new class of $CO_2RR$ electrocatalyst derived from bulk tin (Sn) and copper (Cu) over high surface area carbonaceous support. Electro-catalysts, according to one embodiment, are active even for low temperature aqueous application. Depending on the metal loading, these catalysts have compositions of stable and highly dispersed single atom of metal M (M=Sn or Cu) or metal particle of Sn or Cu with uniform size decorated inside of carbonaceous material. According to some embodiments, various high surface area, carbon supports have been used to prepare electro-catalysts containing Sn and Cu based transition metal centers from the form of single atom to size-controlled uniform metal cluster using an ALM method. In addition, both carbons have high fraction of microporosity over other carbon such as XC72 or EC600. Not limited by the hypothesis, the microporosity will help the retention of $CO_2RR$ reaction intermediates and C—C coupling, therefore leading to higher $CO_2$ to $C_3$ product conversion.

As described herein, the mixing of LiOH-M mixture is with a carbonaceous support. The carbonaceous support has a porous structure, such as having a surface area of greater than 1200 $m^2/g$, such as, 1200-2000 $m^2/g$ including all ranges there in. In one embodiment, the carbonaceous support can either be a commercial support (e.g., DLC50, BP2000 and EC600 commercial supports) or one synthesized based on high surface area materials (e.g., carbon derived from high surface precursors such as zeolites, metal-organic frameworks, or other similar materials). BET specific surface areas of LiOH-treated DLC50, BP2000 and EC600 were determined to be 1870 cm2 g-1, 1487 cm2 g-1, 1210 cm2 g-1, respectively. For the pore distribution of these three carbon supports, DLC50 is dominated by micropores, BP2000 and EC600 are dominated by macropores and mesopores. Depending on the combination of metal loading and surface properties of the carbon support, these electro-catalysts are demonstrated to be highly efficient with high selectivity at low overpotentials and stable in promoting $CO_2$ to glycerol during electrocatalytic $CO_2RR$. For Sn, the loading may be in the range of 0.5% wt to 20 wt %. Specifically, for metal Sn, the preferred metal loading ranges from 0.5 wt. % to 2 wt. % over DLC50 carbon support, or 10 wt. % to 20 wt. % over EC600 carbon support, or 2 wt. % to 20 wt. % over BP2000 carbon support. For Cu, the loading may be in the range of 0.5% wt to 20 wt %. In one embodiment for metal Cu, the preferred metal loading ranges from 0.4 wt. % to 20 wt. % over DLC 50 carbon support, or 0.4 wt. % to 2 wt. % over BP2000 carbon support, or 0.2 wt. % to 1 wt. % over EC600 carbon support. These combinations of metal loading and over amorphous carbons with different surface areas and morphologies can lead to $CO_2RR$ to glycerol with high FE and low onset voltages at different combination of carbon and metal loading. In another embodiment, the electrochemical potential for the $CO_2RR$ over these catalysts ranges from 0.3 V to 1.5 V over reversible hydrogen electrode (RHE). In the preferred embodiment, the electrochemical potential for the $CO_2RR$ over these catalysts ranges from 0.4 V to 0.8 V RHE. With regard to the tested carbon support materials, the DLC50 material is dominated by micropores, while EC600 and BP2000 are dominated by mesopores and macropores. It is believed that micropores have a nano-space confinement effect. Micropores can absorb and store $CO_2$ in large quantities, and mesopores affect the mass transfer effect of $CO_2$.

In the first step, a selected transition metal such as tin, copper, or some combination thereof is dissolved and dispersed in a heated lithium melt, creating a single-atom or metal cluster dispersion within the liquid lithium, depending the amount of M added. For example, the relative ratio of Cu to Li ranges from 0.5% to 2% and relative ratio of Sn to Li ranges from 4% to 40%. The synthesis proceeds through the dispersion of transition metal within a lithium melt under inert atmosphere without contamination by other element. According to one embodiment, the transition metals applicable in $CO_2RR$ lithium-melt electrocatalysts include Sn, Cu, or any transition metal known to be dissolvable in molten lithium and to promote carbon dioxide electro-catalytic reduction.

The second step proceeds by rapid quenching lithium melt to ambient temperature to form lithium-M amalgam. In one embodiment, quenching is carried out in the glovebox filled with argon gas over metal plate such as stainless-steel plate. Quenching from molten lithium-M amalgam to solid lithium-M amalgam typically takes less than 10 seconds during the conversion from molten lithium. During such step, metal M is "frozen" in the form of single-atom or metal cluster dispersion within the solid lithium.

The third step proceeds by exposing the lithium-M amalgam in moisture air under ambient pressure to convert lithium metal to lithium hydroxide. To accelerate the conversion, the relative humidity can be ranged from 20% to 100%. During the process, M remains in the form of single-atom or metal cluster dispersion within the solid matrix of lithium hydroxide.

The fourth step processes by thoroughly mixing the lithium hydroxide containing embedded M in the form single-atom or metal cluster with carbonaceous support, followed by rinsing with water to wash away soluble lithium hydroxide while keeping M over the carbon substrate as the final catalyst. The weight ratio of containing M LiOH to that of amorphous carbon depends on the designated loading of final M over the carbon. For example, to prepare 2 wt. % Sn over the carbon support, the weight of Sn/LiOH containing 4 wt. % Sn to the weight of carbon will be 0.5:1. During the washing step, the water dissolves lithium hydroxide to form concentrated alkaline solution, which subsequently oxidize the carbon surface to form surface functional groups such as —OH, —COOH, —CO groups, promoting the binding of M and M cluster in the new catalyst. The specific surface area of the carbon support can range from 1000-2500 $m^2/g$ or higher, in one embodiment 1200 to 2000 $m^2/g$. The carbon support can be those from the commercial support such as BLACK PEARLS® 2000 (BP2000), Ketjenblack EC600 (EC600), or NORIT® A SUPRA DLC 50 (DLC50), or synthesized carbon materials with similar high surface area and microporosity. As used herein, "decorated" refers to a uniformly distributed single atoms or metal clusters present throughout the carbonaceous material from the outside to the inside of the porous material.

In one embodiment, the $CO_2RR$ catalyst is utilized in the formation of isopropanol. In one embodiment, the $CO_2RR$ conversion selectivity and onset potential can be altered by the combination of Sn loading and the selection of the carbon supports containing high fraction of the microporosity, such as DLC 50 and BP 2000. Not limited by the hypothesis, the microporosity will help the retention of $CO_2RR$ reaction intermediates and C—C coupling, therefore leading to higher $CO_2$ to $C_3$ product conversion. For example, the FE approaches 90% at low onset potential of 0.6 V was observed over the Sn catalyst containing 2 wt %

Sn over BP2000 carbon support. Alternatively, FE>90% can also be achieved with Cu catalyst at 0.4% metal loading over DLC 50 carbon support.

These catalysts can be made into inks for further processing applications such as preparation of membrane electrode assembly. The catalysts have the following advantages: 1) active and stable in aqueous media, 2) high selectivity as well as Faradaic efficiency achievable by controlling electrochemical potential, 3) easy application to surfaces as well as thin films or on substrates; and 4) using low cost, earth abundant transition metal materials. Unlike the prior art of preparing $CO_2$ catalysts, nitrogen containing carbon supports are not required in preparing $CO_2RR$ catalysts. Thus, one embodiment, relates to a nitrogen-free carbon support or nitrogen-free organic solution process. Furthermore, the transfer of catalytic center containing M to the support is carried out at room temperature. Conventional high temperature activation as well as expensive chemical processing post metal dispersion is no longer necessary. Overcoming low product selectivity and low Faradaic efficiency for $CO_2RR$ to 3-carbon organic molecules over the existing electro-catalysts is a major challenge and is accomplished for embodiments described herein, the described $CO_2RR$ electrocatalysts, according to one embodiment, show high selectivity towards single product formation as well as high Faradaic efficiency toward the formation of glycerol, a three carbon organics.

Unlike many prior art $CO_2RR$ catalyst synthesis which use electroplating or metal inorganic and organic based precursor chemistry, the catalyst derived from the current invention, according to one embodiment, uses Li-melt solution chemistry synthesis and therefore can be easily scaled-up. In addition to the advantage of producing single atom supported over the high surface carbon, the current invention can also generate catalyst containing micro-crystallites with uniform size in the dimension of nanometers by simply increasing the metal loading during lithium amalgam preparation. This allows for easy application to porous substrates, or electrode surfaces without the need for advanced processing techniques.

Another embodiment of the current invention is to control the $CO_2RR$ conversion product by changing the operating potential, as will be demonstrated by the examples given below.

Electrocatalysts prepared as described herein have several advantages over that of prior art, including 1) high FE, 2) high selectivity for desired chemical species, 3) high aqueous stability, and 4) controllable product output by controlling operating potential as well as metal loading.

Electrocatalysts in accordance with embodiments herein exhibit high stability in aqueous media as well as under high overpotentials. The high surface area carbon support allows for increased stability, as carbon does not easily degrade at low overpotentials. The high surface area also allows for segregation of metal single atoms and nano-particles, leading to continuous and reliable Faradaic efficiency as well as product selectivity.

The process of preparing lithium-melt catalysts used as electrocatalysts according to some embodiments can be further elucidated by the following examples. Experiments loaded different wt. % Cu on three different carbon supports, including EC600, BP200, DLC50, and measured the electrocatalytic $CO_2RR$ performance. The FE of glycerol showed a decreasing trend with increasing copper loadings on the three different carbon supports. The FE of glycerol reaches a maximum of approximately 91 when 0.4 wt. % copper is supported on DLC50. Further, results showed the impact of different wt. % loading of Sn on three different carbon supports, including EC600, BP200, DLC50, on the measured the electrocatalytic $CO_2RR$ performance. The FE of glycerol decreased with the increase of tin loading on the three different carbon supports, while the FE of isopropanol increased. The FE of glycerol reaches a maximum of approximately 89% when 2 wt. % Sn was supported on BP2000. As the loading of Sn continued to increase, the faradaic efficiency of glycerol decreased, while that of isopropanol increased, and the FE of isopropanol reached a maximum value of about 76% at 20 wt. %.

Figure 12:
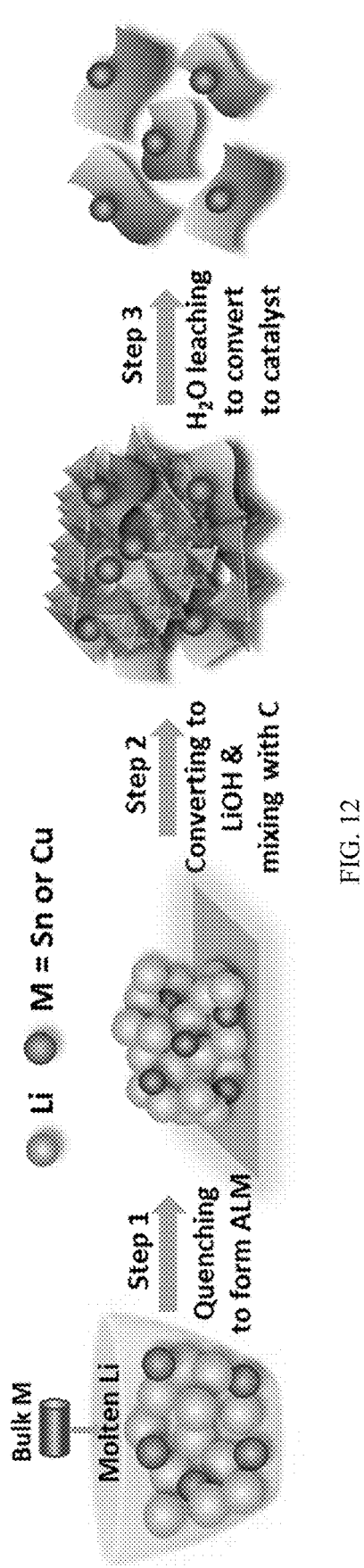
FIG. 12 shows schematics of preparing Sn or Cu $CO_2RR$ catalyst over different carbon supports using lithium-metal amalgam approach according to the current invention.

Example 11. A schematic presentation of Li-melt-based electro-catalyst for $CO_2RR$ is shown in FIG. 12. Synthesis of single atoms/clusters is carried out in an inert atmosphere glovebox. Using a crucible, lithium was heated to above its melting point of 180.5° C. and kept below its boiling point of 1330° C., to which a relative amount of Sn or Cu was added. An ultrasonic homogenizer is used to ensure a uniform dispersion of metal single atoms/clusters while the lithium melt is maintained for between 1 and 3 hours. Formation of a solid solution is achieved by rapidly quenching the melt onto a clean stainless steel plate to solidify the melt without aggregation of metal components. Once the Li—Sn or Li—Cu melt solid cools, the solid is removed from the glovebox before being cut into small pieces. After Li is slowly converted to LiOH under the humidified air, the ensuing Sn or Cu single atoms/clusters/LiOH materials are combined and mixed thoroughly with the desired amount of carbon support. The LiOH was leached out with copious amounts of double-distilled water leaving the Sn or Cu single atoms/clusters embedded in the amorphous carbon support. The resulting powder was collected and used to make an ink.

The activity of the catalyst is evaluated by H-cell using carbon dioxide purged potassium bicarbonate solution electrolyte. Activity of catalysts is measured through cyclic voltammetry and compared to prior art. Glycerol and other chemicals generated in the liquid phase is collected. The product composition as well as Faradaic efficiency are evaluated using a combination of NMR.

Example 12. A Sn/C $CO_2RR$ catalyst (Sn/BP2000-2) synthesized according to the steps described in Example 11. Specifically, 0.5763 mol of lithium (99.9% Sigma-Aldrich) was added into a zirconium crucible and heated to 320° C. to form molten lithium. Then, 1.348 mmol of Sn foil (99.9% Alfa-Aesar) were added into the molten lithium. An ultrasonic homogenizer was used to ensure a homogeneous dispersion of the bulk Sn foil into single atoms and prevents them from precipitation and re-aggregation in molten Li while the molten lithium was maintained at 320° C. for 3 hours. The melted metals were then quickly poured onto a clean 316-stainless steel plates to quench to solid solution. After cooling, the Sn-in-Li amalgam was taken out from the glovebox in ambience, and was cut into small pieces, which were then slowly converted from Li to LiOH under humidified air at ambient temperature. The obtained Sn in LiOH powder was homogeneously mixed with 7.48 g carbon black (BP2000) support by grinding the mixture with an agate mortar and pestle. The resulting mixture was filtered with copious amount of de-ionized water to leach off LiOH. Finally, the filtered carbon-Sn mixture was dried under vacuum at 60° C. for 24 h to form 2 wt % Sn over BP2000, named as Sn/BP2000-2.

A catalyst ink was prepared by adding 5 mg Sn/BP2000-2 into solution of 25 mg of Nafion® (5% in alcohols, Sigma) and 900 mg of methanol. The resulting solution was sonicated for 60 minutes to ensure full dispersion of the electrocatalyst. About 20 microliters of the solution was applied to a carbon paper electrode with a surface area of 1.0 cm2 in droplet. The catalyst was tested at H-cell with $CO_2$ saturated bicarbonate solution (pH 6.8). Chronoamperometry was employed at –0.4 V to –0.8 V at 0.1 V intervals to test the catalyst stability while collecting converted hydrocarbons using NMR analysis.

Figure 13:
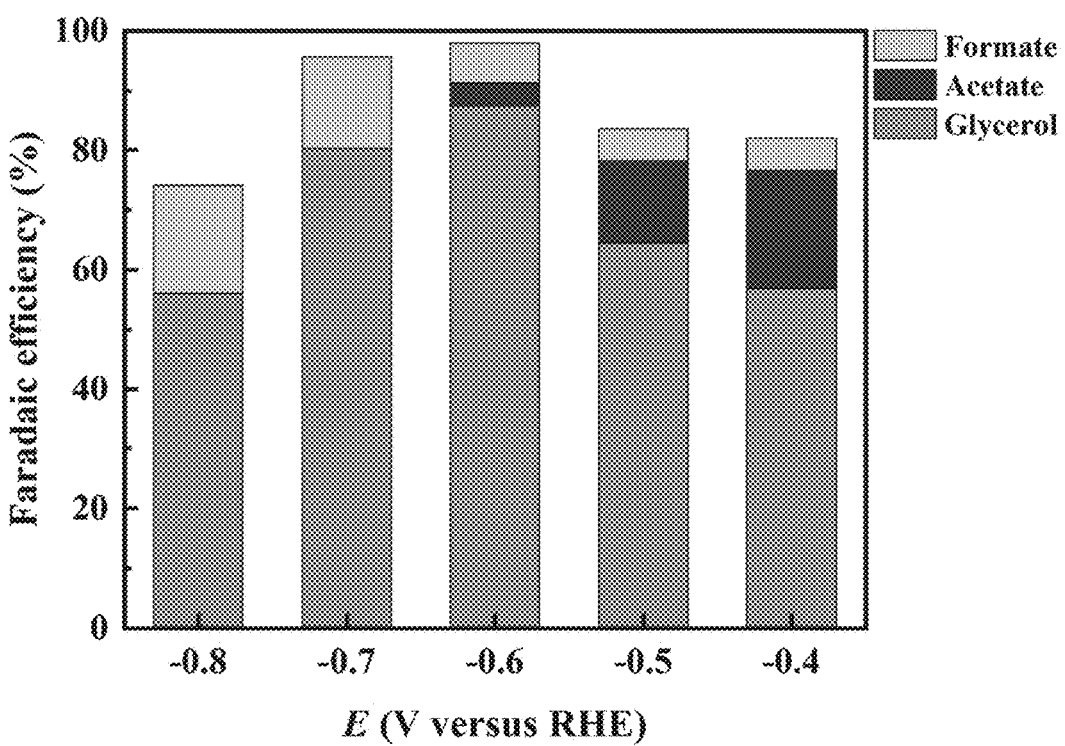
FIG. 13 shows FEs and the product distribution at different cell potential of $CO_2RR$ electrocatalysis over the catalyst (Sn/BP2000-2) according to Example 12.

FE of $CO_2RR$ was calculated according to the Equation 1 set forth previously. FIG. 13 shows the FEs and the different product distribution at various polarization potentials of $CO_2RR$ electrocatalysis over the catalyst Sn/BP2000-2. As can be seen, the catalyst achieved higher than 87% FE for converting $CO_2$ to glycerol at 0.6 V (RHE).

Figure 14:
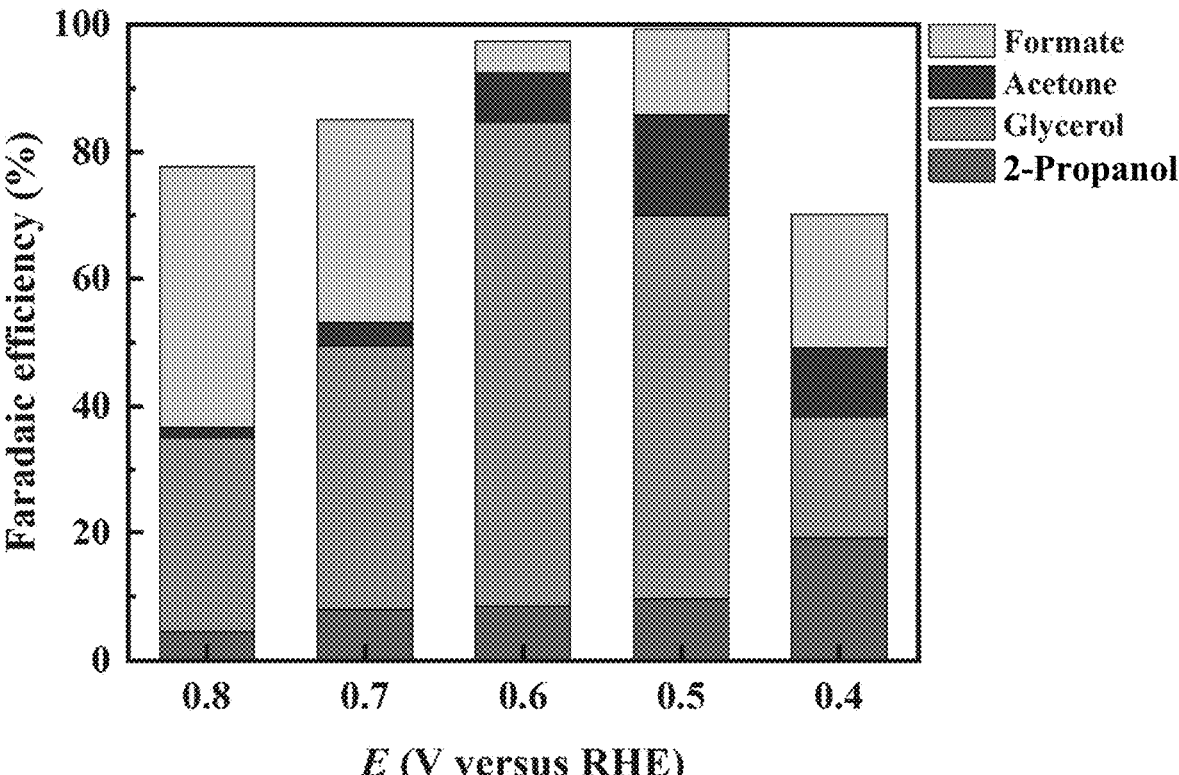
FIG. 14 shows FEs and the product distribution at different cell potential of $CO_2RR$ electrocatalysis over the catalyst (Sn/EC600-20) according to Example 13.

Example 13. A $CO_2RR$ catalyst synthesized according to the steps described in Example 1 and Example 12 except that 1.348 mmol (~160 mg) of Sn foil (99.9% Alfa-Aesar) were added into the 0.5763 mol of molten lithium. The final catalyst has 20 wt % Sn over EC600, named as Sn/EC600-20. FIG. 14 shows the FEs and the different product distribution including glycerol, acetate, formate and isopropanol at various polarization potentials of $CO_2RR$ electrocatalysis over the catalyst Sn/EC600-20. As can be seen, the catalyst achieved higher than 72% FE for converting $CO_2$ to glycerol at 0.6 V (RHE).

Figure 15:
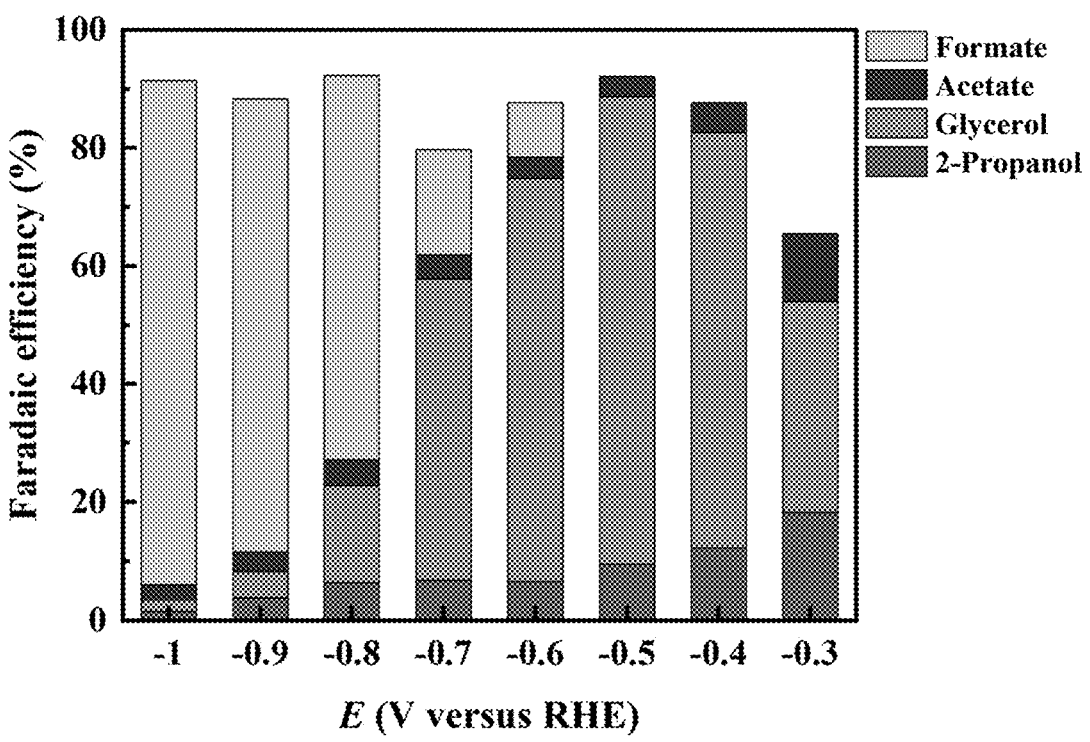
FIG. 15 shows FEs and the product distribution at different cell potential of $CO_2RR$ electrocatalysis over the catalyst (Sn/DLC-2) according to Example 14.

Example 14. A Sn/C $CO_2RR$ catalyst synthesized according to the steps described in Example 11 and Example 12 except that 1.348 mmol (~160 mg) of Sn foil (99.9% Alfa-Aesar) were added into the 0.5763 mol of molten lithium. The final catalyst has 2 wt % Sn over carbon DLC50, named as Sn/DLC-2. FIG. 15 shows the FEs and the different product distribution at various polarization potentials of $CO_2RR$ electrocatalysis over the catalyst Sn/DLC-2. As can be seen, the catalyst achieved higher than 79% FE for converting $CO_2$ to glycerol at –0.5 V (RHE).

Figure 16:
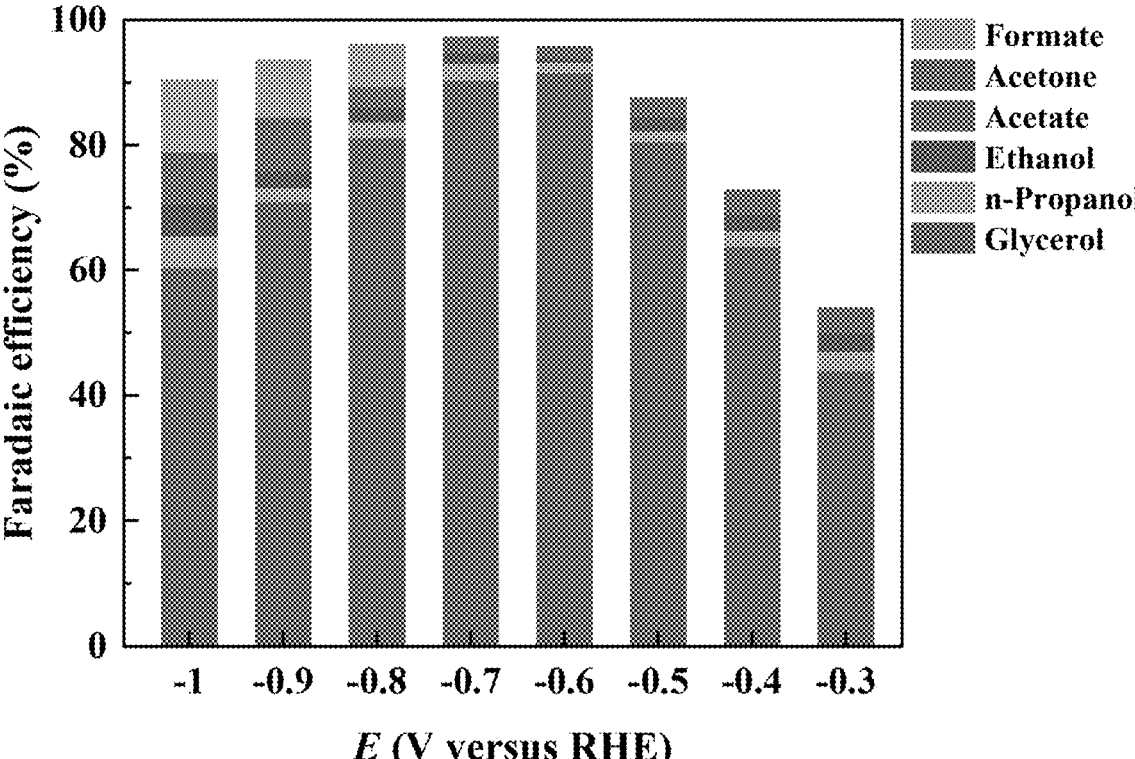
FIG. 16 shows FEs and the product distribution at different cell potential of $CO_2RR$ electrocatalysis over the catalyst (Cu/DLC50-0.4) according to Example 15.

Example 15. A carbon (DLC50) supported copper $CO_2RR$ catalyst was synthesized according to the procedure described in Example 11 and Example 12. Briefly, 0.6295 mmol (~40 mg) of Cu wire (99.9% Alfa-Aesar) were added into 0.5763 mol of molten lithium. The final catalyst has 0.4 wt % In over DLC50, named as Cu/DLC50-0.4. FIG. 16 shows the FEs and the different product distribution at various polarization potentials of $CO_2RR$ electrocatalysis over the catalyst Cu/DLC50-0.4. As can be seen, the catalyst achieved higher than 90% FE for converting $CO_2$ to glycerol at –0.6 V (RHE).

Figure 17:
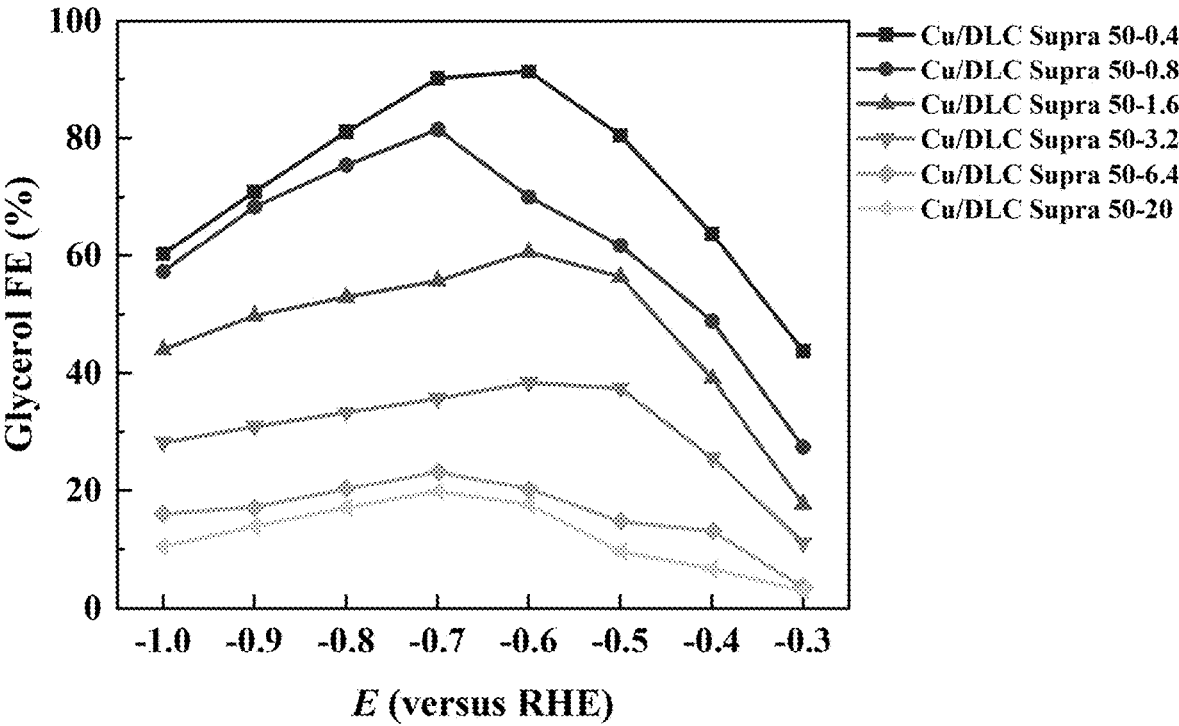
FIG. 17 shows FEs as the function of cell potential measured over Cu/DLC catalysts with different Cu loadings, according to Example 16.

Example 16. Several Cu based $CO_2RR$ catalysts supported by DLC50 carbon were prepared with Cu loading ranging from 0.4% to 20% according to the procedure described in Example 11 and Example 15. FIG. 17 shows their $CO_2RR$ FEs toward glycerol formation at different polarization potentials. As can be seen, the catalyst Cu/DLC50-0.4 achieved the highest FE>90% at 0.6 V. With the increase of copper loading, the FE towards glycerol conversion decreased precipitately, indicating the importance of high metal dispersion in controlling high selectivity to a single product formation.

Isopropanol Production.

In one embodiment, the electrocatalysts for direct conversion of $CO_2$ to isopropanol. Some embodiments relate to a new class of $CO_2RR$ electrocatalyst derived from bulk tin (Sn) over high surface area carbonaceous support. Electrocatalysts, according to one embodiment, are active even for low temperature aqueous application. Depending on the metal loading, these catalysts have compositions of stable and highly dispersed single atom and metal cluster of Sn with uniform size decorated on the carbonaceous material. According to some embodiments described in the examples below, two high surface area, carbon supports, BP2000 and DLC50, have been used to prepare electro-catalysts containing Sn based transition metal centers from the form size-controlled uniform metal cluster using an ALM method. In addition, both carbons have high fraction of microporosity over other carbon such as XC72 or EC600. Not limited by the hypothesis, the microporosity will help the retention of $CO_2RR$ reaction intermediates and C—C coupling, therefore leading to higher $CO_2$ to $C_3$ product conversion.

As described herein, the mixing of LiOH-M mixture is with a carbonaceous support. The carbonaceous support has a porous structure, such as having a surface area of greater than 1200 m²/g, such as, 1200-2000 m²/g including all ranges therein. In one embodiment, the carbonaceous support can either be a commercial support (e.g., DLC50, BP2000 and EC600 commercial supports) or one synthesized based on high surface area materials (e.g., carbon-derived from high surface precursors such as zeolites, metal-organic frameworks, or other similar materials). BET specific surface areas of LiOH-treated DLC50, BP2000 and EC600 were determined to be 1870 cm²/g, 1487 cm²/g, 1210 cm²/g, respectively. For the pore distribution of these three carbon supports, DLC50 is dominated by micropores, BP2000 and EC600 are dominated by macropores and mesopores. These electrocatalysts are demonstrated to be highly efficient with high selectivity at low overpotentials and stable in promoting $CO_2$ to isopropanol during electrocatalytic $CO_2RR$. Specifically, Sn metal supported over high surface area, high micro-porosity amorphous carbons can lead to $CO_2RR$ to isopropanol with high FE and low onset voltages at different combination of carbon and metal loading.

With regard to the tested carbon support materials, the DLC50 material is dominated by micropores, while EC600 and BP2000 are dominated by mesopores and macropores. Its believed that micropores have a nano-space confinement effect. Micropores can absorb and store $CO_2$ in large quantities, and mesopores affect the mass transfer effect of $CO_2$.

In a first step, a selected transition metal, such as tin, or some combination thereof, is dissolved and dispersed in a heated lithium melt, creating a single-atom or metal cluster dispersion within the liquid lithium, depending the amount of M added. For example, the relative ratio of Sn to Li ranges from 4% to 40%. The synthesis proceeds through the dispersion of transition metal within a lithium melt under inert atmosphere without contamination by other element. According to one embodiment, the transition metals applicable in $CO_2RR$ lithium-melt electrocatalysts include Sn or any transition metal known to be dissolvable in molten lithium and to promote carbon dioxide electro-catalytic reduction.

A second step proceeds by rapid quenching lithium melt to ambient temperature to form lithium-M amalgam. During such step, metal M is "frozen" in the form of single-atom or metal cluster dispersion within the solid lithium. The quenching is carried out in the glovebox filled with argon gas over metal plate such as stainless-steel plate. Quenching from molten lithium-M amalgam to solid lithium-M amalgam typically takes less than 10 seconds during the conversion from molten lithium.

A third step proceeds by exposing the lithium-M amalgam in moisture air to convert lithium metal to lithium hydroxide. To accelerate the conversion, the relative humidity can be ranged from 20% to 100%. During the process, M remains in the form of single-atom or metal cluster dispersion within the solid matrix of lithium hydroxide.

A fourth step proceeds by thoroughly mixing the lithium hydroxide containing embedded M in the form single-atom or metal cluster with carbonaceous support, followed by rinsing with water to wash away soluble lithium hydroxide while keeping M over the carbon substrate as the final catalyst. The weight ratio of containing M LiOH to that of amorphous carbon depends on the designated loading of final M over the carbon. For example, to prepare 2 wt. % Sn over the carbon support, the weight of Sn/LiOH containing 4 wt. % Sn to the weight of carbon will be 0.5:1. During the washing step, the water dissolves lithium hydroxide to form concentrated alkaline solution, which subsequently oxidize the carbon surface to form surface functional groups such as —OH, —COOH, —CO groups, promoting the binding of M and M cluster in the new catalyst. The specific surface area of the carbon support can range from 1000 $m^2/g$ to 2500 $m^2/g$ or higher. The carbon support can be those from the commercial support such as BLACK PEARLS® 2000 (BP2000), or NORIT® A SUPRA DLC 50 (DLC50), or synthesized carbon materials with similar high surface area and microporosity. Herein "decorated" refers to a uniformly distributed single atoms or metal clusters present throughout the carbonaceous material from the outside to the inside of the porous material.

In one embodiment, the $CO_2RR$ catalyst is utilized in the formation of isopropanol. In one embodiment, the $CO_2RR$ conversion selectivity and onset potential can be altered by the combination of metal loading and the selection of the carbon support. In a preferred embodiment, Sn metal loading ranges from 10 wt. % to 40 wt. % over DLC50 carbon support. In another preferred embodiment, Sn metal loading ranges from 5 wt. % to 20 wt. % over BP2000 carbon support. In another embodiment, the FEs of $CO_2RR$ over these catalysts have the electrochemical potential ranging from 0.3 V to 0.8 V (RHE). In a preferred embodiment, the electrochemical potential for the $CO_2RR$ over Sn/DLC50 catalyst ranges from 0.3 V to 0.7 V RHE and the electrochemical potential for the $CO_2RR$ over Sn/BP2000 catalyst ranges from 0.4 V to 0.7 8 RHE, respectively. For example, the FE approaches 50% at low onset potential of 0.3 V was observed over the Sn catalyst containing 20 wt % Sn over DLC Supra carbon support and FE~80% can also be achieved with the same catalyst at 0.5 V.

These catalysts can be easily made into inks for further processing applications such as preparation of membrane electrode assembly. The catalysts have the following advantages: 1) active and stable in aqueous media, 2) high selectivity as well as FE achievable by controlling electrochemical potential, 3) easy application to surfaces as well as thin films or on substrates; and 4) using low cost, earth abundant transition metal materials. Unlike the prior art of preparing $CO_2$ catalysts, nitrogen containing carbon supports are not required in preparing $CO_2RR$ catalysts. Thus, one embodiment, relates to a nitrogen-free carbon support or nitrogen-free organic solution process. Furthermore, the transfer of catalytic center containing M to the support is carried out at room temperature. Conventional high temperature activation as well as expensive chemical processing post metal dispersion is no longer necessary. Overcoming low product selectivity and low Faradaic efficiency for $CO_2RR$ to 3-carbon organic molecules over the existing electro-catalysts is a major challenge and is accomplished for embodiments described herein, the described $CO_2RR$ electrocatalysts, according to one embodiment, show high selectivity towards single product formation as well as high Faradaic efficiency toward the formation of isopropanol, a three carbon organics.

Unlike many prior art $CO_2RR$ catalyst synthesis which use electroplating or metal inorganic and organic based precursor chemistry, the catalyst derived from the current invention, according to one embodiment, uses Li-melt solution chemistry synthesis and therefore can be easily scaled-up. In addition to the advantage of producing single atom supported over the high surface carbon, the current invention can also generate catalyst containing micro-crystallites with uniform size in the dimension of nanometers by simply increasing the metal loading during lithium amalgam preparation. This allows for easy application to porous substrates, or electrode surfaces without the need for advanced processing techniques.

Another embodiment of the current invention is to control the $CO_2RR$ conversion product by changing the operating potential, as will be demonstrated by the examples given below.

Electrocatalysts prepared as described herein have several advantages over that of prior art, including 1) high Faradaic efficiency, 2) high selectivity for desired chemical species, 3) high aqueous stability, and 4) controllable product output by controlling operating potential as well as metal loading.

Electrocatalysts in accordance with embodiments herein exhibit high stability in aqueous media as well as under high overpotentials. The high surface area carbon support allows for increased stability, as carbon does not easily degrade at low overpotentials. The high surface area also allows for segregation of metal single atoms and nano-particles, leading to continuous and reliable Faradaic efficiency as well as product selectivity.

The process of preparing lithium-melt catalysts used as electrocatalysts according to some embodiments can be further elucidated by the following examples.

Example 17. A schematic presentation of Li-melt-based electro-catalyst for $CO_2RR$ is shown in FIG. 12. Synthesis of single atoms/clusters is carried out in an inert atmosphere glovebox. Using a crucible, lithium was heated to above its melting point of 180.5° C. and kept below its boiling point of 1330° C., to which a relative amount of Sn or Cu was added. An ultrasonic homogenizer is used to ensure a uniform dispersion of metal single atoms/clusters while the lithium melt is maintained for between 1 and 3 hours. Formation of a solid solution is achieved by rapidly quenching the melt onto a clean stainless steel plate to solidify the melt without aggregation of metal components. Once the Li—Sn or Li—Cu melt solid cools, the solid is removed from the glovebox before being cut into small pieces. After Li is slowly converted to LiOH under the humidified air, the ensuing Sn or Cu single atoms/clusters/LiOH materials are combined and mixed thoroughly with the desired amount of carbon support. The LiOH was leached out with copious amounts of double-distilled water leaving the Sn or Cu single atoms/clusters embedded in the amorphous carbon support. The resulting powder was collected and used to make an ink.

The activity of the catalyst is evaluated by H-cell using carbon dioxide purged potassium bicarbonate solution electrolyte. Activity of catalysts is measured through cyclic voltammetry and compared to prior art. Glycerol and other chemicals generated in the liquid phase is collected. The product composition as well as Faradaic efficiency are evaluated using a combination of NMR.

Example 18. A Sn/C $CO_2RR$ catalyst (Sn/BP2000-20) synthesized according to the steps described in Example 17. Specifically, 0.5763 mol of lithium (99.9% Sigma-Aldrich) was added into a zirconium crucible and heated to 320° C. to form molten lithium. Then, 1.348 mmol of Sn foil (99.9%

Alfa-Aesar) were added into the molten lithium. An ultrasonic homogenizer was used to ensure a homogeneous dispersion of the bulk Sn foil into single atoms and prevents them from precipitation and re-aggregation in molten Li while the molten lithium was maintained at 300° C. for 2 hours. The melted metals were then quickly poured onto a clean 316-stainless steel plates to quench to solid solution. After cooling, the Sn-in-Li amalgam was taken out from the glovebox in ambience, and was cut into small pieces, which were then slowly converted from Li to LiOH under humidified air at ambient temperature. The obtained Sn in LiOH powder was homogeneously mixed with 1.28 g carbon black (BP2000) support by grinding the mixture with an agate mortar and pestle. The resulting mixture was filtered with copious amount of de-ionized water to leach off LiOH. Finally, the filtered carbon-Sn mixture was dried under vacuum at 60° C. for 24 hours to form 20 wt % Sn over BP2000, named as Sn/BP2000-20.

A catalyst ink was prepared by adding 5 mg Sn/BP2000-20 into solution of 25 mg of Nafion® (5% in alcohols, Sigma) and 900 mg of methanol. The resulting solution was sonicated for 60 minutes to ensure full dispersion of the electrocatalyst. About 20 microliters of the solution was applied to a carbon paper electrode with a surface area of 1.0 cm2 in droplet. The catalyst was tested at H-cell with $CO_2$ saturated bicarbonate solution (pH 6.8). Chronoamperometry was employed at –0.4 V to –0.8 V at 0.1 V intervals to test the catalyst stability while collecting converted hydrocarbons using NMR analysis.

FE of $CO_2RR$ was calculated according to the Equation 1. FIG. 18 shows the FEs and the different product distribution at various polarization potentials of $CO_2RR$ electrocatalysis over the catalyst Sn/BP2000-20. As can be seen, the catalyst achieved higher than combined 60% FE for converting $CO_2$ to glycerol and isopropanol at 0.6 V (RHE).

Example 19. A $CO_2RR$ catalyst synthesized according to the steps described in Examples 17 and 18 except that 1.348 mmol (~160 mg) of Sn foil (99.9% Alfa-Aesar) were added into the 0.5763 mol of molten lithium. The final catalyst has 20 wt % Sn over DLC Supra, named as Sn/DLC Supra-20. FIG. 19 shows the FEs and the different product distribution including glycerol, acetate, formate and isopropanol at various polarization potentials of $CO_2RR$ electrocatalysis over the catalyst Sn/DLC Supra-20. As can be seen, the catalyst achieved FE of nearly 80% for converting CO2 to isopropanol at 0.6 V (RHE).

Example 20. Sn/C $CO_2RR$ catalysts synthesized according to the steps described in Example 17 and Example 18 except that Sn loadings over DLC Supra varied from 0.5% to 40%. FIGS. 20A-20F show the FEs over different Sn/DLC Supra-X catalysts with different product distribution at various polarization potentials of $CO_2RR$ electrocatalysis. The catalysts with low Sn loading showed predominated glycerol formation, whereas catalysts of high Sn loading showed more isopropanol formation.

Example 21. Several Sn based $CO_2RR$ catalysts supported by DLC supra carbon were prepared with Sn loading ranging from 0.4-20% according to the procedure described in Examples 17 and 20. FIG. 21 shows their $CO_2RR$ FEs toward isopropanol formation at different polarization potentials. As can be seen, the catalyst Cu/DLC Supra-20 achieved the highest FE~80% at 0.6 V. With the increase of tin loading, the FE towards glycerol conversion decreased precipitately whereas the FE to isopropanol increased.

Definitions

As used herein, the singular forms "a," "an" and "the" include plural referents unless the context clearly dictates otherwise. Thus, for example, the term "a member" is intended to mean a single member or a combination of members, "a material" is intended to mean one or more materials, or a combination thereof. As used herein, the terms "about" and "approximately" generally mean plus or minus 10% of the stated value. For example, about 0.5 would include 0.45 and 0.55, about 10 would include 9 to 11, about 1000 would include 900 to 1100.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Other substitutions, modifications, changes and omissions may also be made in the design, operating conditions and arrangement of the various exemplary embodiments without departing from the scope of the present invention.

While this specification contains many specific implementation details, these should not be construed as limitations on the scope of any inventions or of what may be claimed, but rather as descriptions of features specific to particular implementations of particular inventions. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

We claim:
1. A method of synthesizing a catalyst comprising:
adding a catalytic metal selected from the group consisting of Sn and Cu in its metallic form to molten lithium metal, wherein a ratio of Cu to Li ranges from 0.5% to 2% or the relative ratio of Sn to Li ranges from 4% to 40%;
atomically dispersing the catalytic metal in the molten lithium metal;
forming a lithium catalytic metal-solid;
converting a portion of lithium in the lithium catalytic metal solid to lithium hydroxide forming a catalytic metal-lithium hydroxide solid;
mixing said catalytic metal-lithium hydroxide solid with a conductive support material to form a mixture, the conductive support material being carbonaceous with a porous network and having catalytic metal decorated throughout the porous network with a specific surface area of 1200 to 2000 $m^2/g$;

removing lithium hydroxide from the mixture leaving a mixture of catalytic metal and the conductive support material; and drying the mixture of catalytic metal and the conductive support material to produce the catalyst containing the catalytic metal atomically dispersed over the conductive support material.

2. The method of claim 1, wherein converting the portion of the lithium-catalytic metal solid to catalytic metal-lithium hydroxide solid comprises reacting lithium in the lithium catalytic metal solid with moist air.

3. The method of claim 2, further comprising mixing the catalytic metal-lithium hydroxide solid with the conductive support material using a mechanical method.

4. The method of claim 1, wherein the molten lithium metal has a temperature of 300° C. or less.

5. The method of claim 1, wherein removing the lithium hydroxide comprises a drop-wise washing of the catalytic metal-lithium metal hydroxide solid with water thereby removing lithium.

6. The method of claim 5, wherein the washing comprises forming an alkaline water solution and modifying the carbonaceous support with oxygenated species serving as anchoring sites for the catalytic metal.

7. The method of claim 1, wherein the catalytic metal comprises Cu.

8. The method of claim 1, wherein a loading range for the catalytic metal on the conductive support material is 0.2 wt % to 20 wt %.

9. The method of claim 8, wherein the loading range is 0.2 wt % to 1 wt %.

10. The method of claim 8, wherein the loading range is 0.4 wt % to 2 wt %.

11. The method of claim 1, wherein the catalytic metal comprises Sn.

12. The method of claim 11, wherein a loading range for the catalytic metal on the conductive support material is 0.5 wt % to 20 wt %.

13. The method of claim 11, wherein the loading range is 0.5 wt % to 2 wt %.

14. The method of claim 11, wherein the loading range is 10 wt % to 20 wt %.

15. The method of claim 11 wherein the loading range is 10 wt % to 40 wt %.

16. A process for forming glycerol comprising:

providing a catalyst having catalytic metal, comprising Sn or Cu, atomically dispersed as 0.2 wt % to 20 wt % over a carbonaceous conductive support material having a surface area of 1200-2000 $m^2/g$;

exposing carbon dioxide to the catalyst; and forming glycerol.

17. The process of claim 16, wherein the glycerol is formed at a Faradaic efficiency of at least 90%.

18. A process for forming isopropanol comprising:

providing a catalyst having catalytic metal, comprising Sn atomically dispersed over a carbonaceous conductive support material having a surface area of 1200-2000 $m^2/g$;

exposing carbon dioxide to the catalyst; and forming isopropanol.

19. The process of claim 18, wherein the isopropanol is formed at a Faradaic efficiency of at least 80%.

* * * * *